(12) United States Patent
Lyle et al.

(10) Patent No.: US 6,363,290 B1
(45) Date of Patent: Mar. 26, 2002

(54) INTERACTIVE CONTROL SYSTEMS FOR MEDICAL PROCESSING DEVICES

(75) Inventors: Guy A. Lyle, Lake Zurich; William H. Cork, Lake Bluff; Mark C. Weber, West Dundee; David E. Morrow, Chicago, all of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/595,536

(22) Filed: Jun. 16, 2000

Related U.S. Application Data

(63) Continuation of application No. 09/356,272, filed on Jul. 16, 1999, which is a division of application No. 08/680,437, filed on Jul. 15, 1996, now Pat. No. 5,956,023, which is a continuation of application No. 08/337,639, filed on Nov. 10, 1994, now Pat. No. 5,581,687.

(51) Int. Cl.[7] .............................................. G05B 15/00
(52) U.S. Cl. ................................ 700/83; 700/9; 700/17
(58) Field of Search ................................ 345/326–333, 345/771, 792; 707/100–104, 104.1; 210/767, 739; 700/9, 17, 83

(56) References Cited

U.S. PATENT DOCUMENTS

| | | | |
|---|---|---|---|
| 4,396,976 A | * 8/1983 | Hyatt | 700/1 |
| 4,613,866 A | 9/1986 | Blood | 342/448 |
| 4,866,638 A | 9/1989 | Cosentino et al. | 345/763 |
| 4,995,412 A | 2/1991 | Smith et al. | 135/67 |
| 5,041,992 A | 8/1991 | Cunningham et al. | 345/641 |
| 5,108,889 A | 4/1992 | Smith | 435/4 |
| 5,121,477 A | 6/1992 | Koopmans et al. | 345/762 |
| 5,228,123 A | 7/1993 | Heckel | 345/762 |
| 5,327,529 A | 7/1994 | Fults et al. | 345/762 |
| 5,347,629 A | 9/1994 | Barrett et al. | 345/762 |
| 5,353,401 A | 10/1994 | Iizawa et al. | 345/763 |
| 5,366,896 A | 11/1994 | Margrey et al. | 436/48 |
| 5,639,382 A | 6/1997 | Brown | 210/739 |
| 5,676,841 A | 10/1997 | Brown | 210/739 |
| 5,681,273 A | 10/1997 | Brown | 604/6.07 |
| 5,730,883 A | 3/1998 | Brown | 210/739 |
| 5,759,413 A | 6/1998 | Brown | 210/767 |

* cited by examiner

*Primary Examiner*—Paul P. Gordon
*Assistant Examiner*—Ella Colbert
(74) *Attorney, Agent, or Firm*—Daniel D. Ryan; Bradford R. L. Price; Michael C. Mayo

(57) ABSTRACT

A controller provides an abstract, "virtual" interface between the software based applications resident in the controller and the hardware elements of the fluid processing system. The controller also provides a straightforward yet very interactive dual region user interface.

4 Claims, 17 Drawing Sheets

INTERACTIVE CONTROL SYSTEMS FOR MEDICAL PROCESSING DEVICES

This application is a continuation of 09/356272 filed Jul. 16, 1999 which is a division of 08/680437 filed Jul. 15, 1996 now U.S. Pat. No. 5,956,023 which is a continuation of 08/337639 filed Nov. 10, 1994 now U.S. Pat. No. 5,581,687

FIELD OF THE INVENTION

The invention relates to control systems and user interfaces for fluid processing systems, such as blood processing systems and the like.

BACKGROUND OF THE INVENTION

Today people routinely separate whole blood by centrifugation into its various therapeutic components, such as red blood cells, platelets, and plasma.

These and other medical processing devices are often controlled using microprocessors with resident program software. The microprocessors also usually include some type of interface through which the operator views and comprehends information regarding the operation of the fluid processing systems.

As the operational and performance demands upon such fluid processing systems become more complex and sophisticated, the need exists for simplifying the control hierarchy of microprocessor based control systems.

As the operational and performance demands also become more complex and sophisticated, the need exists for straightforward, yet higher interactive user interfaces.

SUMMARY OF THE INVENTION

One aspect of the invention addresses the need for simple yet effective control systems. This aspect provides an abstract, "virtual" interface between the software based applications resident in the controller and the hardware elements of the fluid processing system. High level process software resident in the controller communicates with lower level implementing process software in an instrument manager, instead of communicating directly with hardware elements. In this way, the intermediate instrument manager isolates or "hides" all hardware-specific commands from the high left control software. The data flow between the instrument manager and the hardware elements of the system is invisible to the high level software.

The creation of the virtual interface between high level process software and the hardware elements provides considerable flexibility in adding or modifying the process software.

Another aspect of the invention addresses the need for straightforward yet highly interactive user interfaces. This aspect of the invention provides an interface having two distinct viewing regions, called the status region and the working region. Preferably, the two viewing regions are fixed in relative position and unchanging in size on the interface screen. This provides continuity and consistency to the appearance of the interface, even as the functional hardware of the system cycle through different processing modes. The uniformity and consistency of the dual viewing regions of the interface reduce operator confusion and the likelihood of error.

According to the invention, the status region and the working region are each dedicated to different types and levels of information. Nevertheless, the two regions are always displayed simultaneously to provide the operator views of both high level "big picture" information (in the status region) and low level "detailed" information (in the working region).

The two viewing regions also allow the operator to use the interface quickly to find and select among detailed procedures, functions, and options during system operation, or to perform off-line functions, without losing touch with the overall status of the ongoing procedure. The two viewing regions permit the operator to navigate what is in reality a multiple-level menu structure to attend to details on one menu level, without necessarily moving stepwise up and down the menu structure and without losing the ability to, on command, immediately jump between higher and lower menu levels.

The features and advantages of the invention will become apparent from the following description, the drawings, and the claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
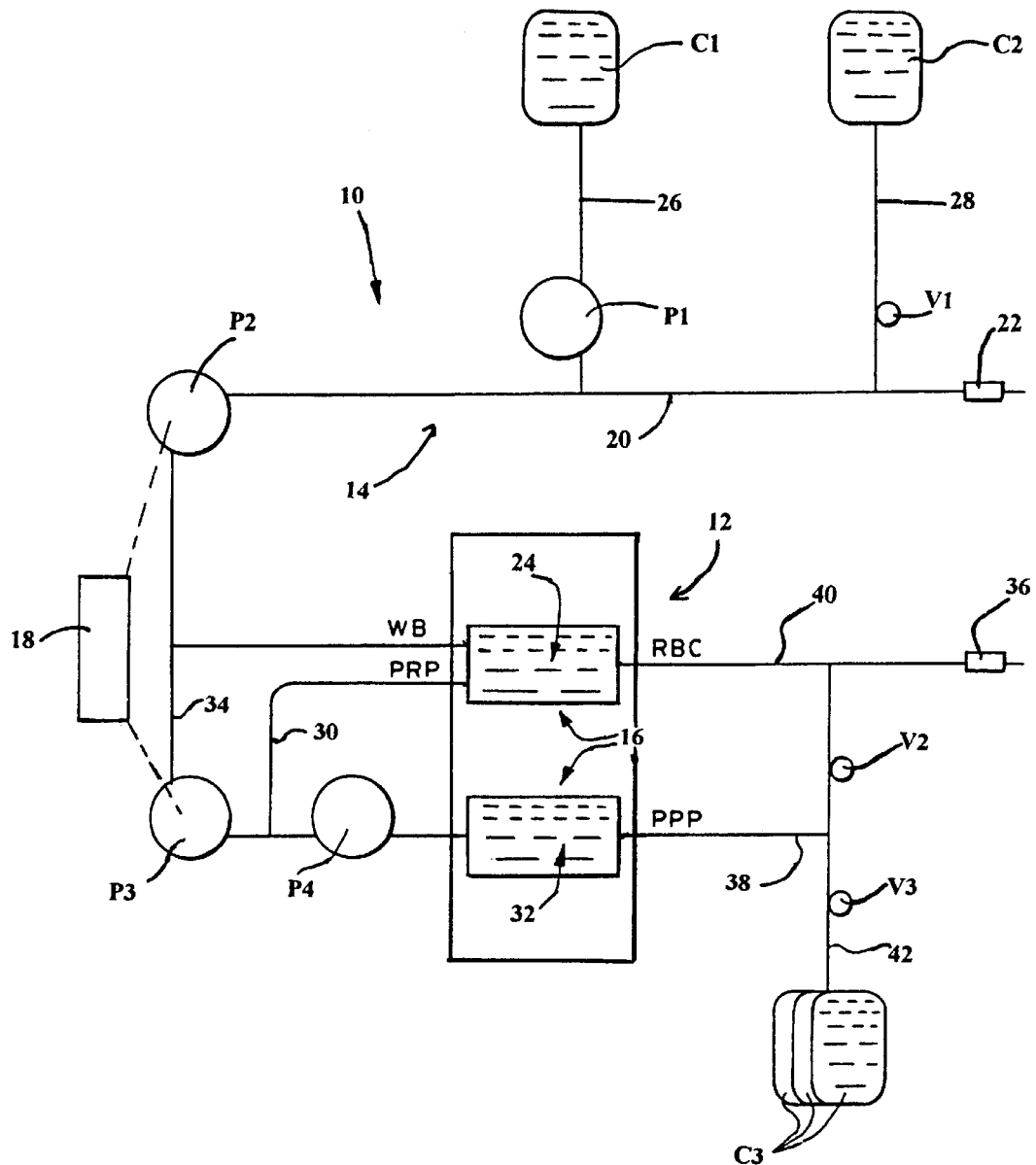
FIG. 1 is a diagrammatic view of a dual needle platelet collection system that includes a controller that embodies the features of the invention.

FIG. 1 shows in diagrammatic form a fluid processing system 10. The system 10 can be used for processing various fluids. The system 10 is particularly well suited for processing fluids for medical purposes, like whole blood and other suspensions of biological cellular materials. Accordingly, the illustrated embodiment shows the system 10 used for this purpose.

I. The Separation System

The system 10 includes an arrangement of durable hardware elements, The hardware elements will vary according to the nature and type of processing system. In the context of processing whole blood, the hardware elements will include a centrifuge 12, in which whole blood (WB) is separated into its various therapeutic components, like platelets, plasma, and red blood cells (RBC). The hardware elements will also include various pumps, which are typically peristaltic (designated P1 to P4); and various in line clamps and valves (designated V1 to V3). Of course, other types of hardware elements will typically be present, which FIG. 1 does not show, like solenoids, pressure monitors, and the like.

The system 10 typically also includes some form of a disposable fluid processing assembly 14 used in association with the hardware elements.

In the illustrated blood processing system 10, the assembly 14 includes a two stage processing chamber 16. In use, the centrifuge 12 rotates the processing chamber 16 to centrifugally separate blood components.

The construction of the two stage processing chamber 16 can vary. For example, it can take the form of double bags, like the processing chambers shown in Cullis et al. U.S. Pat. No. 4,146,172. Alternatively, the processing chamber 16 can take the form of an elongated two stage integral bag, like that shown in Brown U.S. Pat. No. U.S. 5,529,691.

In the illustrated blood processing system 10, the processing assembly 14 also includes an array of flexible tubing that forms a fluid circuit. The fluid circuit conveys liquids to and from the processing chamber 16. The pumps P1–P4 and the valves V1–V3 engage the tubing to govern the fluid flow in prescribed ways. The fluid circuit further includes a number of containers (designated C1 to C3) to dispense and receive liquids during processing.

A controller 18 governs the operation of the various hardware elements to carry out one or more processing tasks using the assembly 14. The invention specifically concerns important attributes of the controller 18.

The system 10 can be configured to accomplish diverse types of blood separation processes. FIG. 1 shows the system 10 configured to carry out an automated two needle platelet collection procedure.

In a collection mode, a first tubing branch 20 and the whole blood inlet pump P2 direct WB from a draw needle 22 into the first stage 24 of the processing chamber 16. Meanwhile, an auxiliary tubing branch 26. meters anticoagulant from the container C1 to the WB flow through the anticoagulant pump P1.

The container C2 holds saline solution. Another auxiliary tubing branch 28 conveys the saline into the first tubing branch 20, via the in line valve V1, for use in priming and purging air from the system 10 before processing begins. Saline solution is also introduced again after processing ends to flush residual components from the assembly 14 for return to the donor.

Anticoagulated WB enters and fills the first stage 24 of the processing chamber 24. There, centrifugal forces generated during rotation of the centrifuge 12 separate WB into red blood cells (RBC) and plateletrich plasma (PRP).

The PRP pump P4 operates to draw PRP from the first stage 24 of the processing chamber 16 into a second tubing branch 30 for transport to the second stage 32 of the processing chamber 16. There, the PRP is separated into platelet concentrate (PC) and plateletpoor plasma (PPP).

The system 10 includes a recirculation tubing branch 34 and an associated recirculation pump P3. The processing controller 18 operates the pump P3 to divert a portion of the PRP exiting the first stage 24 of the processing chamber 16 for remixing with the WB entering the first stage 24 of the processing chamber 16.

As WB is drawn into the first chamber stage 24 for separation, the illustrated two needle system simultaneously returns RBC from the first chamber stage 24, along with a portion of the PPP from the second chamber stage 32, to the donor through a return needle 36 through tubing branches 38 and 40 and in line valve V2.

The system 10 also collects PC in some of the containers C3 through tubing branches 38 and 42 and in line valve V3 for storage and therapeutic use. The system 10 can also collect PPP in some of the containers C3 through the same fluid path.

II. The System Controller

The controller 18 carries out the overall process control and monitoring functions for the system 10 as just described.

Figure 2:
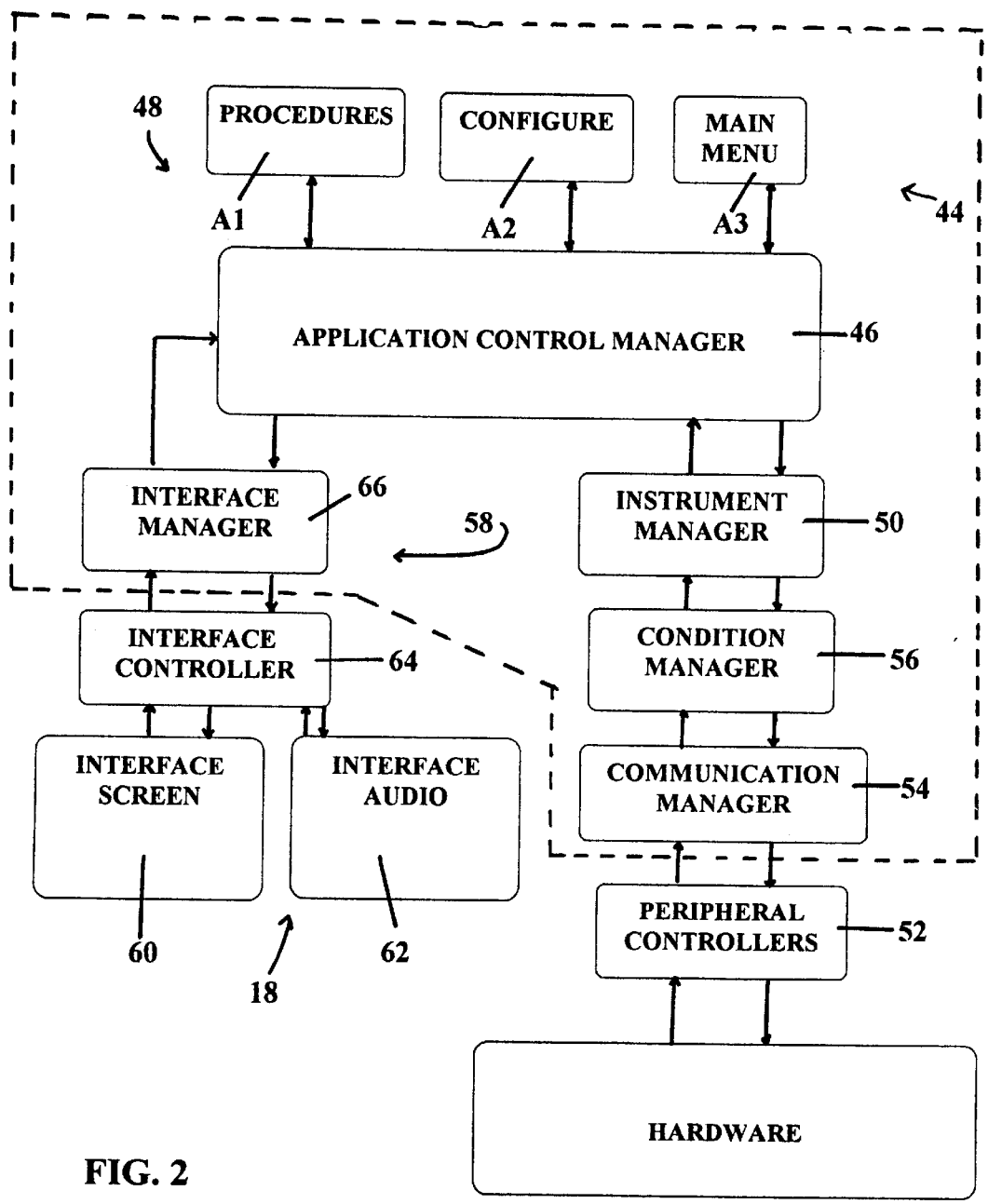
FIG. 2 is a diagrammatic flow chart view of the controller and associated interface that embodies the features of the invention.

In the illustrated and preferred embodiment (see FIG. 2), the controller comprises a main processing unit (MPU) 44. In the preferred embodiment, the MPU 44 comprises a type 68030 microprocessor made by Motorola Corporation, although other types of conventional microprocessors can be used.

In the preferred embodiment, the MPU 44 employs conventional real time multi-tasking to allocate MPU cycles to processing tasks. A periodic timer interrupt (for example, every 5 milliseconds) preempts the executing task and schedules another that is in a ready state for execution. If a reschedule is requested, the highest priority task in the ready state is scheduled. Otherwise, the next task on the list in the ready state is schedule.

A. Functional Hardware Control

The MPU 44 incudes an application control manager 46. The application control manager 46 administers the activation of a library 48 of control applications (designated A1 to A3). Each control application A1–A3 prescribes procedures for carrying out given functional tasks using the system hardware (e.g., the centrifuge 12, the pumps P1–P4, and the valves V1–V3) in a predetermined way. In the illustrated and preferred embodiment, the applications A1–A3 reside as process software in EPROM's in the MPU 44.

The number of applications A1–A3 can vary. In the illustrated and preferred embodiment, the library 48 includes at least one clinical procedure application A1. The procedure application A1 contains the steps to carry out one prescribed clinical processing procedure. For the sake of example in the illustrated embodiment, the library 48 includes a procedure application A1 for carrying out the dual needle platelet collection process, as already generally described in connection with FIG. 1. Of course, additional procedure applications can be, and typically will be, included. For example, the library 48 can include a procedure application for carrying out a conventional single needle platelet collection process.

In the illustrated and preferred embodiment, the library 48 also includes at least one additional, non-procedure application. The non-clinical procedural application contains the procedures to carry out a system configuration or support utility. For the sake of example in the illustrated embodiment, the library 48 includes a configuration application A2, which contains the procedures for allowing the operator to configure the default operating parameters of the system 10. The library 48 also includes a main menu application A3, which coordinates the selection of the various applications A1–A3 by the operator, as will also be described in greater detail later.

Of course, additional non-clinical procedure applications can be, and typically will be, included. For example, the library 48 can include a diagnosis application, which contains the procedures aiding service personnel in diagnosing and troubleshooting the functional integrity of the system, and a system restart application, which performs a full restart of the system, should the system become unable to manage or recover from an error condition.

An instrument manager 50 also resides as process software in EPROM's in the MPU 44. The instrument manager 50 communicates with the application control manager 46. The instrument manager 50 also communicates with low level peripheral controllers 52 for the pumps, solenoids, valves, and other functional hardware of the system.

Figure 3:
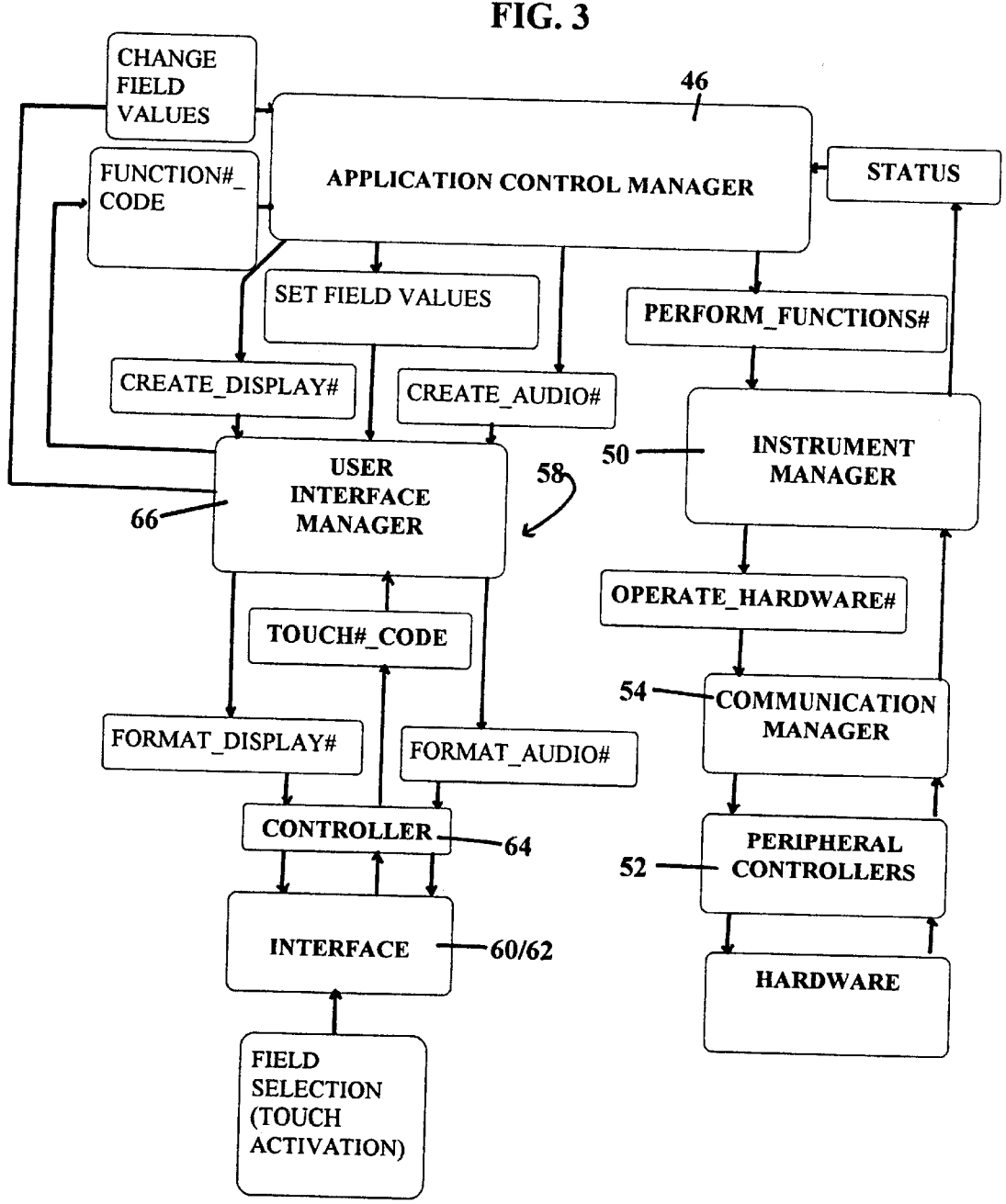
FIG. 3 is another diagrammatic view of the controller and associated interface shown in FIG. 2, and further showing the command and status flow hierarchy.

As FIG. 3 shows, the application control manager 46 sends specified Perform_Function# commands in abstract form to the instrument manager 50, as called up by the activated application A1–A3. In response to these abstract commands, the instrument manager 50 identifies the peripheral controller or controllers 52 for performing the function and compiles hardware-specific operate_Hardware# commands into the command tables for the particular peripheral controllers 52. The peripheral controllers 52 communicate directly with the hardware to implement the hardware-specific commands generated by the instrument manager 50, causing the hardware to operate in a specified way to carry out the abstract Perform_Function# commands. A communication manager 54 manages low-level protocol and communications between the instrument manager 50 and the peripheral controllers 52.

As FIG. 3 also shows, the instrument manager 50 also conveys back to the application control manager 46 status data about the operational and functional conditions of the processing procedure. The status data is expressed in terms of, for example, fluid flow rates, sensed pressures, and fluid volumes measured.

The application control manager 46 processes and uses the status data in various ways. In one way, the application control manager 46 transmits selected status data for display to the operator, as will be described later. In another way, the application control manager 46 monitors operational and functional conditions using the status data to detect abnormal system conditions requiring operator intervention or system shutdown, as will also be described in greater detail later.

In the preferred embodiment (see FIG. 2), the MPU 44 also includes a condition manager 56 that resides in the data flow path between the instrument manager 50 and the communications manager 54. The condition manager 56 also monitors status data and other operational states of the hardware to detect abnormal conditions that are either not detected or are left uncorrected by the application control manager 46. Upon detecting such abnormal conditions, the condition manager 56 provides fail-safe support by suspending system operation. Further details of this fail-safe function and other related aspects of the controller 18 will be described later.

The described control hierarchy creates an abstract, "virtual" interface between the applications resident in the application control manager 46 and the hardware elements of the system 10. The high level process software resident in the application control manager 46 communicates with lower level implementing process software in the instrument manager 50, instead of communicating directly with hardware elements. In this way, the intermediate instrument manager 50 isolates or "hides" all hardware-specific commands from the application control manager 46. The applications pass abstract Perform_Function# commands to the instrument manager 50, and the instrument manager 50 converts these abstract commands into the specific Operate_Hardware# commands unique to the particular hardware elements, all without further participation by the procedure applications A1–A3 themselves. The data flow between the instrument manager 50 and the hardware elements of the system 10 is invisible to the activated application A1–A3.

The creation of the virtual interface between high level process software and the hardware elements provides considerable flexibility in adding or modifying the process software of the high level applications A1–A3 for controlling hardware functions. New or modified process software for the applications need only to include specified hardware-non-specific abstract Perform_Function# commands to gain immediate linkage to the virtual hardware interface. Likewise, addition or modification of specific hardware requires only changes to the low level process software of the instrument manager 50. Because of the virtual interface, hardware changes require minimal changes to the high level software in the application control manager 46.

As described above, the instrument manager 50 forms a part of the same MPU in which the application control manager 46 resides. Alternatively, because of the virtual nature of the interface, the instrument manager 50 can reside on a separate processing unit.

B. User Interface Control

In the illustrated embodiment, the MPU 44 also includes an interactive user interface 58. The interface 58 allows the operator to view and comprehend information regarding the operation of the system 10. The interface 58 also allows the operator to select applications residing in the application control manager 46, as well as to change certain functions and performance criteria of the system 10.

The interface 58 includes an interface screen 60 and, preferably, an audio device 62. The interface screen 60 displays information for viewing by the operator in alpha-numeric format and as graphical images. The audio device 62 provides audible prompts either to gain the operator's attention or to acknowledge operator actions.

In the illustrated and preferred embodiment, the interface screen 60 also serves as an input device. It receives input from the operator by conventional touch activation, as will be described later. Alternatively or in combination with touch activation, a mouse or keyboard could be used as input devices.

An interface controller 64 communicates with the interface screen 60 and audio device 62. The interface controller 64, in turn, communicates with an interface manager 66, which in turn communicates with the application control manager 46. The interface controller 64 and the interface manager 66 reside as process software in EPROM's in the MPU 44.

In use, the application control manager 46 sends to the interface manager 66 specified field values reflecting selected status data received from the instrument manager 50. The application control manager 46 also sends to the interface manager 66 prescribed abstract Create_Display# and Create_Audio# commands called for by the activated application.

The interface manager 66 processes these field values and the abstract Create_Display# commands to generate specific Format_Display# commands. The Format_Display# commands control the particular format, attributes, and protocols necessary to create, refresh, and close the visual display on the interface screen 60.

Likewise, the interface manager 66 processes the abstract Create_Audio# commands to generate specific Format_Audio# commands. The Format_Audio# commands dictate the format and attributes of the audio output called for by the activated application.

The interface manager 66 conveys the processed Format_Display# and _Audio# commands to the interface controller 64. The interface controller 64 provides low level control functions that draw boxes and lines, forms text or graphical characters, and provides the formatting ant attributes of the display on the interface screen 60. The interface controller 64 also provides low level control functions that drive the audio device 62 based upon Format_Audio# commands received from the interface manager 66.

The interface controller 64 also accepts Field#_Select commands generated by touch activation of the interface screen 60, as will be described in greater detail later. The interface controller 64 passes this touch activated input to the interface manager 66 in the form of Touch#_Codes. The interface manager 66 processes the Touch#_Codes to the application control manager 46, either as function codes or as changed field values. The application control manager 46 implements the function codes or changed field values and passes them to the instrument manager 50. Further details of this will be provided later.

This control hierarchy also creates an abstract, "virtual" interface between the functional processors of the controller 18 and the interface 58. The high process software of the interface manager 66 isolates and "hides" all formatting and protocol issues used in creating the interface 58 from the applications used to control hardware functions of the system 10. The process software of the applications A1–A3, through the application control manager 46, pass abstract field values and Create_Display# and Create_Audio# commands to the interface manager 66. The process software of the interface manager 66 converts these abstract commands into the specific commands that control the textual and graphic formats and audio formats of the operator interface 58, without further participation by the procedure applications A1–A3 themselves. The data flow between the interface manager 66 and the interface controller 64 is invisible to the data flow between the application control manager 46 and the instrument manager 50.

This control hierarchy lends further flexibility in adding or modifying applications for controlling hardware functions. New or modified applications need only to include textual field value outputs and the prescribed Create_Display# or Create_Audio# commands to gain immediate linkage to the operator interface.

(i) Interface Screen Format

In the illustrated and preferred embodiment (see FIG. 4), the Format_Display# commands of the interface manager 66 formats information for display on the interface screen 60 in two distinct viewing regions, called the status region 68 and the working region 70. Preferably, the two viewing regions 68 and 70 are fixed in relative position and unchanging in size on the interface screen 60. This provides continuity and consistency to the appearance of the interface 58, even as the functional hardware of the system cycle through different processing modes. The uniformity and consistency of the dual viewing regions 68 and 70 of the interface 58 reduce operator confusion and the likelihood of error.

The status region 68 and the working region 70 are each dedicated to different types and levels of information. Nevertheless, the two regions 68 and 70 are always displayed simultaneously to provide the operator views of both high level "big picture" information and low level "detailed" information.

The working region 70 provides the means for the operator to select and activate any one of the system-resident applications A1–A3. The working region 70 displays all specific procedure-dependent information then called for by the Create_Display# commands generated by the activated application A1–A3. The considerable detail of information displayed in the working region 70 allows the operator to monitor and change the ongoing process in real time.

On the other hand, the status region 68 continuously shows prescribed procedure-dependent information of a more general and "overview" nature, about which a operator routinely needs continuous knowledge and immediate access. The status region 68 continuously displays this general information to keep the operator appraised of the overall status of the ongoing process, even when the operator is using the working region 70 to monitor and change more detailed aspects of the processes. In the illustrated and preferred embodiment, the status region 68 also provides means for the operator to respond to alarms or malfunctions.

The two viewing regions 68 and 70 allow the operator to use the interface 58 quickly to find and select among detailed procedures, functions, and options during system operation, or to perform off-line functions, without losing touch with the overall status of the ongoing procedure. The two viewing regions 68 and 70 permit the operator to navigate what is in reality a multiple-level menu structure to attend to details on one menu level, without necessarily moving stepwise up and down the menu structure and without losing the ability to, on command, immediately jump between higher and lower menu levels.

In the illustrated embodiment, the viewing regions 68 and 70 are vertically separated by a graphical line or line of characters 72, with the status region 68 occupying the upper one-third of the screen 60 and the working region 70 occupying the lower two-thirds of the screen 60. It should be appreciated, however, that the viewing regions 68 and 70 could be separated horizontally in a side by side relationship, and occupy differing proportions of the screen 60.

The status region 68 and the working region 70 display information in fields. The Format_Display# for the particular display that the interface manager 66 generates is composed of a list of such fields specifying, for each field, its location, size, and type in the region and the format of information it contains.

As will be discussed in greater detail later, the fields can formatted as individual touch selectable buttons. The fields can also be formatted as an array of touch selectable button fields, which present a field of choices to the operator.

The fields can also be formatted as blocks comprising alpha or numeric data strings, or textual data comprising multiple lines of line-wrapped, scrollable text, or graphic images. The fields can also be formatted to be bar graph fields, which display numeric format in graphical form.

The interface manager 66 includes constant (ROM-based) structures in look-up table form that store data describing the layout and formatting of all display attributes, including regions, field type, and field location within the regions. The interface manager 66 stores dynamic (RAM-based) structures that describe the present state of the interface display. Upon receiving a given Create_Display# command from the activated application, the interface manager 66 examines the ROM-based table structures and the RAM-based status structures to create or update the RAM-based status structures, as called for by the activated application. The interface manager 66 includes a time-triggered task routine that performs all operations required to periodically update screen 60 and audio outputs. The interface manager 66 sends this processed information to the interface controller 64 for implementation.

The interface manager 66 also holds a Function#_Code associated with each touch selectable button field identified by the Touch#_Code received from the interface controller 64. The Function#_Codes are arranged in constant (ROM-based) look-up table form according to region and field location within the region, as identified by the Touch#_ Code. The interface controller 64 registers the region and field location when a given button is touched, passing this information in the form of a Touch#_Code to the interface manager 66. The interface manager 66 includes a process button utility that awaits and asynchronously processes this information by examining the ROM-based table structure and sending the appropriate Function#_Code to the application control manager 46 for implementation.

Figure 4:
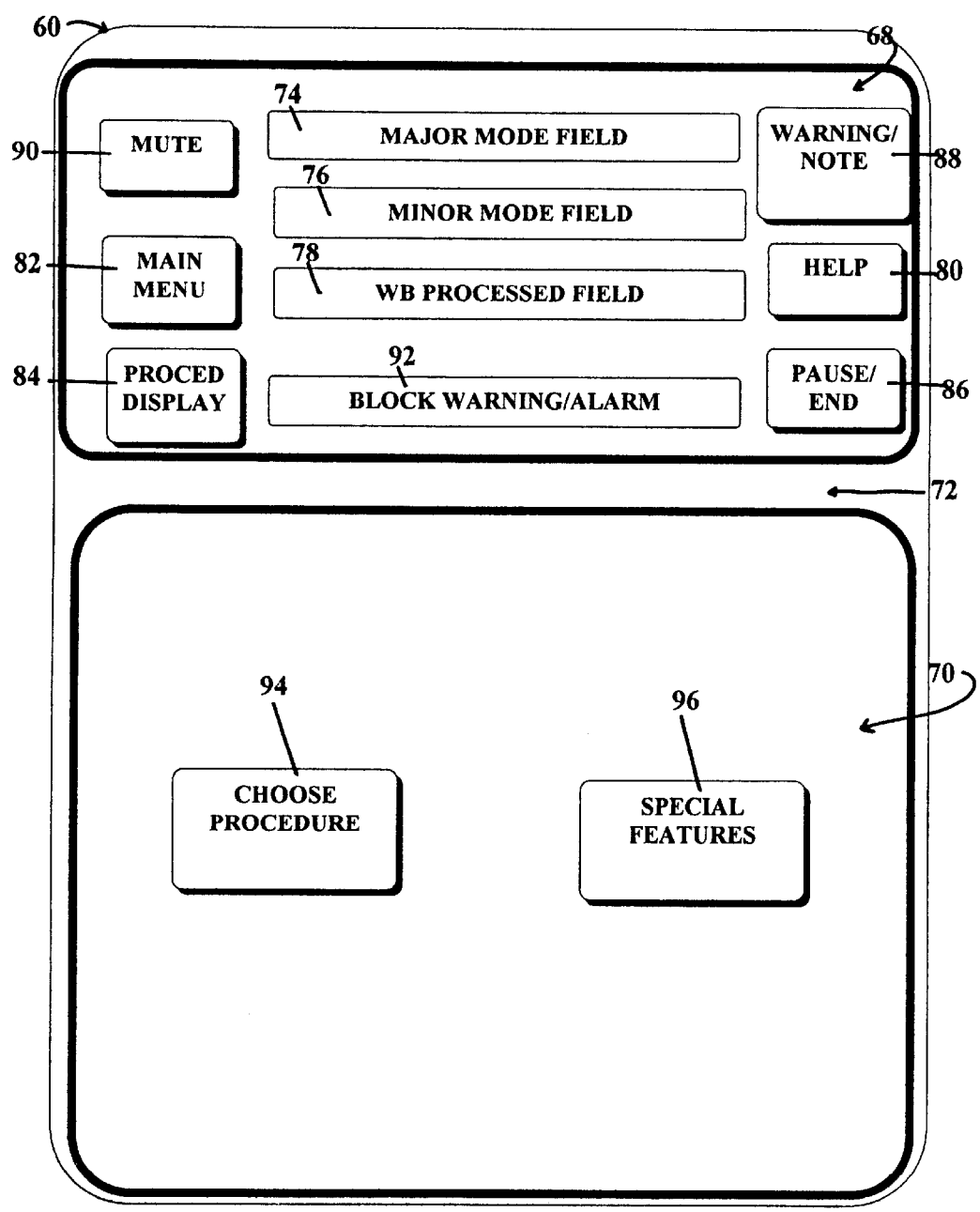
FIG. 4 is a view of the dual region interface that embodies the features of the invention, showing the block and touch activated fields that the interface contains.

The information and format selected for display in the status region 68 and the working region 70 can vary. FIG. 4 shows a preferred implementation.

1. The Status Region

In the illustrated and preferred implementation, the status region 68 includes a three blocks fields 74/76/78 that provide general status information about the procedure then being run.

The MAJOR MODE field 74 contains the description of the clinical procedure activated. For example, the procedure is "Dual Needle Platelet Collection," or any other application selected by the user and resident in the application control manager 46.

The MINOR MODE field 76 contains a one or two word description of the procedure status. For example, for a Dual Needle Platelet Collection, the MINOR MODE field 76 can sequentially display an install mode (for installing disposable elements on the hardware elements); a system check mode (for checking hardware operation before beginning processing); a prime mode (for removing air from the system before processing); a collection mode (for collecting whole blood for processing); a flush and reinfusion mode (for removing residual components from the system for return to the donor after processing); and a so-called wrap-up mode (for removing disposable elements from the hardware elements after processing).

The WB PROCESSED field 78 contains the amount of blood drawn from the donor through the draw pump P2 during processing, expressed numerically in units of ml. The WB PROCESSED field 78 is displayed when the dual needle procedure enters the collection mode and remains displayed until the procedure has ended or is terminated.

In the illustrated and preferred embodiment, the status region 68 also includes an array of touch selectable button fields 80/82/84/86. As before described, the individual button fields 80/82/84/86, when touched, each cause the interface manager 66 to transmit a prescribed function code for implementation by the application control manager 46. The touch selection of a given button field does not alter the display of information in the blocks fields 74/76/78 on the status region 68. Any change in the interface 58 resulting from touch selection of a given button in the status region 68 typically occurs in the working region 70.

When touched, the HELP button field 80 calls up a context-sensitive function that displays in the working region 70 general, largely qualitative information regarding the procedure status displayed in the MINOR MODE field 76.

When touched, the MENU button field 82 calls up a function that causes activation of the main menu application and the resulting display of the Main Menu in the working region 70 (as FIG. 4 shows as a default condition). As will be described in greater detail later, the Main Menu allows the operator to select for activation any application A1–A3 managed by the application control manager 46.

When touched, the PROCEDURE DISPLAY button 84 field calls up a function that displays in the working region 70 the display of specific procedure-dependent information then called for the activated procedure application.

The MENU button field 82 and the PROCEDURE DISPLAY button field 84 in the status region 68 together make possible the rapid selection of other non-clinical procedure applications while a givenclinical procedure application runs, while retaining the ability to immediately return to the particular display of specific procedure-dependent information then called for by the activated clinical procedure, without the need to progress up and down through a menu tree structure or to find one's place in a sequence of menus that are intended to lead the operator stepwise through the procedure from start to finish.

When touched, the PAUSE/END button field 86 calls up a function that immediately pauses any currently operating clinical procedure application. At the same time, the button calls for the display in the working region 70 of the display of specific procedure-dependent information called for by the activated procedure at the time that the PAUSE/END button 86 is activated. At this time, the working region 70 display also preferable includes a RESUME touch activated button field or an END touch activated button field, to give the operator the choice of continuing with the procedure or halting it.

In the illustrated implementation, the block fields 74/76/78 occupy fixed locations in the center of the status region 68. The MENU button field 82 and the PROCEDURE DISPLAY button field 84 occupy fixed locations on the left side, middle and bottom positions, of the status region 68, respectively. The HELP button field 80 occupies a fixed location on the right side, middle position, of the status region 68. The PAUSE/END button field 86 occupies a fixed location on the right side, bottom position, of the status region 68.

The status region 68 also includes context-dependent NOTE/WARNING PROMPT button field 88 that occupies a fixed location on the right side, top position, of the status region 68 when an alarm or warning is active. The NOTE/WARNING PROMPT button field 88 is not displayed when an alarm or warning is not active. A MUTE button field 90 also occupies a fixed location on the left side, top position, of the status region 68 when an alarm is active. A WARNING/ALARM block field also occupies a fixed location on the center, bottom position, of the status region when an alarm is active. Further details of the alarms and the NOTE/WARNING PROMPT and MUTE buttons 88 and 90 and the WARNING ALARM block filed 92 will be described later.

2. The Working Region

In the illustrated and preferred embodiment, the working region 70 shows by default the Main Menu display called for by the main menu application A3. The Main Menu display includes an array of touch selectable button fields 94 and 96, labeled CHOOSE PROCEDURE and SPECIAL FEATURES.

When touched, the CHOOSE PROCEDURE button field 94 calls up a function that displays a Procedure Submenu in the working region 70. The Procedure Submenu lists in an array of touch selectable button fields all clinical procedure applications administered by the application control manager 46, which in the illustrated implementation is the Dual Needle Procedure Application A1. When touched, a procedure application button field calls up a function that directs the application control manager 46 to activate the associated application. The activated application generates its own designated Create_Display# commands, which the interface manager 66 implements to change the display in the working region 70. Further details of this will be provided later.

When touched, the SPECIAL FEATURES button field 96 calls up a function that displays a Special Features Submenu in the working region 70. The Features Submenu lists in an array of touch selectable button fields designed non-clinical procedure specific applications administered by the application control manager 46, which in the illustrated implementation is the Configure System Procedure Application A2. When a given special procedures application button is touched, that application is activated and the display in the working region 70 changes in response to the Create_Display# commands of the activated application. Further details of this will be provided later. According to the protocol established by the interface manager 66 in the preferred implementation, only one display is active at any given time in the status and working regions 68 and 70. The operator can make input selections using the active display, and the interface manager 66 up dates and refreshes the active display with real time information received from the activated application.

Conceptually, working displays on each region 68 and 70 lie on top of each other, with the most recent "active" display lying on top, the first preceding active display laying inactive beneath it, and so on. If the active display is deleted or closed by the activated application, or by one of the functions called by a touch activated button field, without a new Create-Display# command, the interface manager 66 makes the first preceding display visible and active. A display called for by a create display command is placed on top and made active until terminated, closed, or replaced by a successive create display command.

Preferably, the interface manager 66 includes additional RAM-based memory to preformat frequently used displays before displaying them. Such "virtual displays" remain inactive until called for an activated application or by a callable function.

Figure 5:
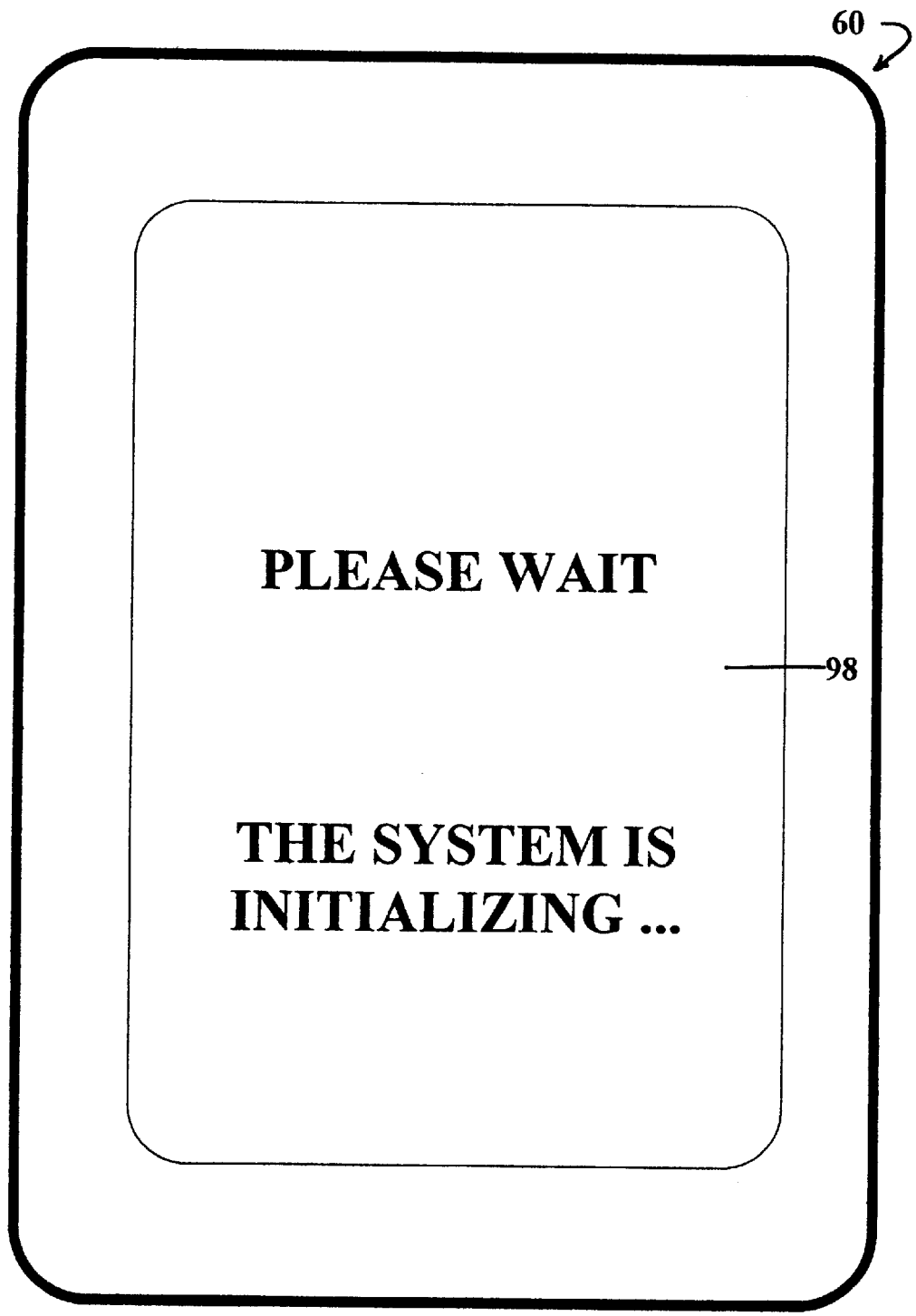
FIG. 5 is a view of the interface shown in FIG. 4 when in a full screen mode.

In the illustrated and preferred embodiment, the interface manager 66 also supports a full screen 60 mode (see FIG. 5), which can be enabled or disabled by any particular application. In the full screen 60 mode, the interface screen 60 includes a single textual or graphical block field 98 forming single display region. The full screen mode can be used, for example, during system start-up, initialization, and some diagnostic modes.

The following example illustrates the operation of the dual region interface.

EXAMPLE

Figure 8:
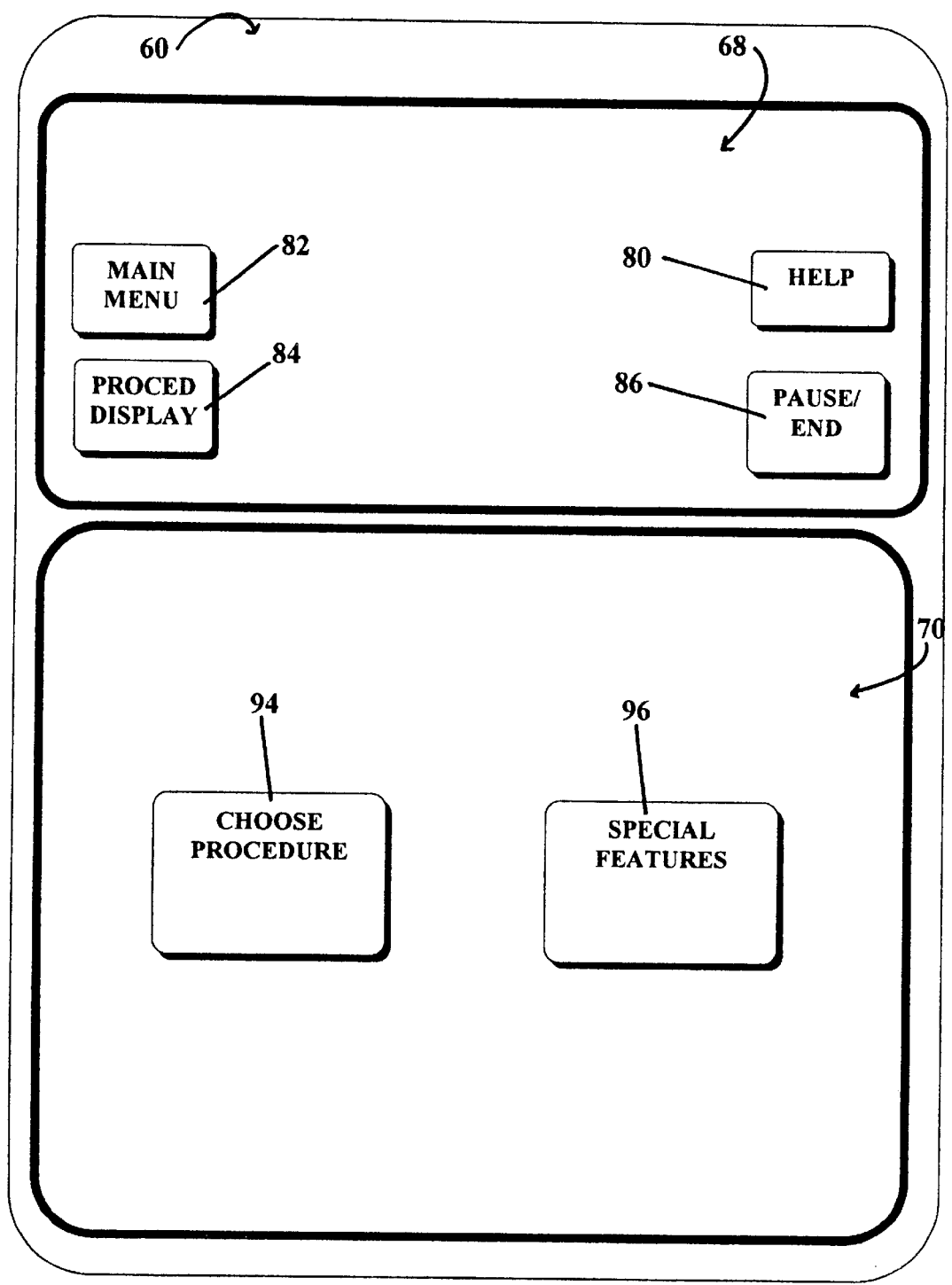
FIG. 8 is a view of the dual region interface in a system start-up default condition, showing the Main Menu in the working region of the interface screen.

FIG. 8 shows the default condition of the dual region interface screen 60 that embodies the features of the invention, as it exists before the selection of a procedure application. The status region 68 is thus free of the MAJOR MODE, MINOR MODE, WB PROCESSED, and BLOCK WARNING/ALARM fields 74/76/78/92 (see FIG. 4 for comparison). In addition, the MUTE and WARNING/NOTE button fields 88 and 90 (also see FIG. 4 for comparison) are also empty. The working region 70 shows the Main Menu, showing a CHOOSE PROCEDURE button field 94 and a SPECIAL FEATURES button field 96 already described.

Figure 9:
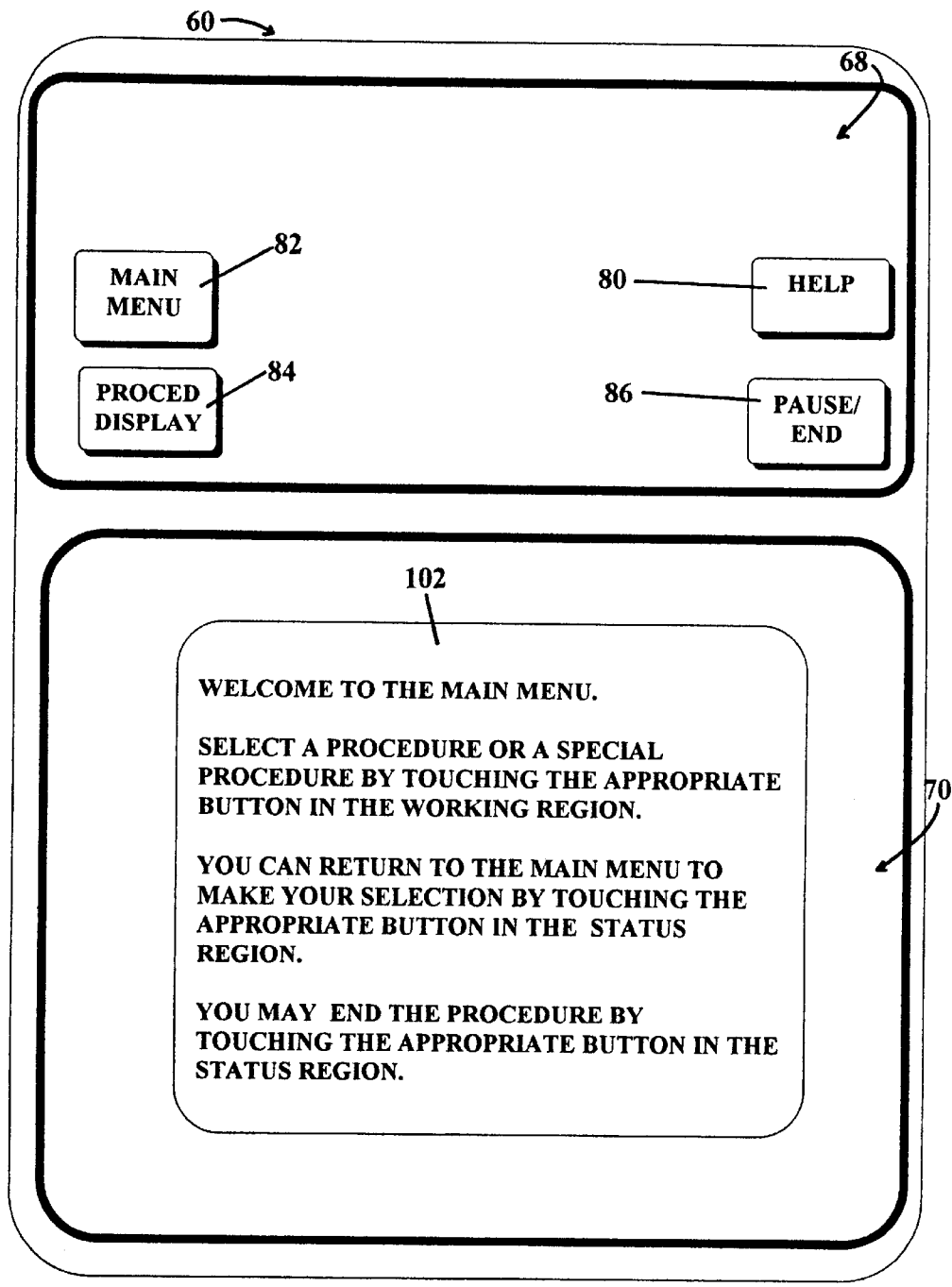
FIG. 9 is a view of the condition of the interface screen with the HELP button activated in the status region when the Main Menu is active in the working region of the screen.

FIG. 9 shows the condition of the dual region interface screen 60, after the operator has selected the HELP button field 80 in the status region 68. The status region 68 shows no change. However, a textual field 102 has been opened in the working region 70, overlying and hiding the Main Menu. The textual field 102 provides general information about the Main Menu and the selection options available in the Main Menu and in the status region 68. By touch selecting the MAIN MENU button 82 in the status region 68, the operator immediately returns to the Main Menu in the working region 70, as FIG. 8 shows.

Figure 10:
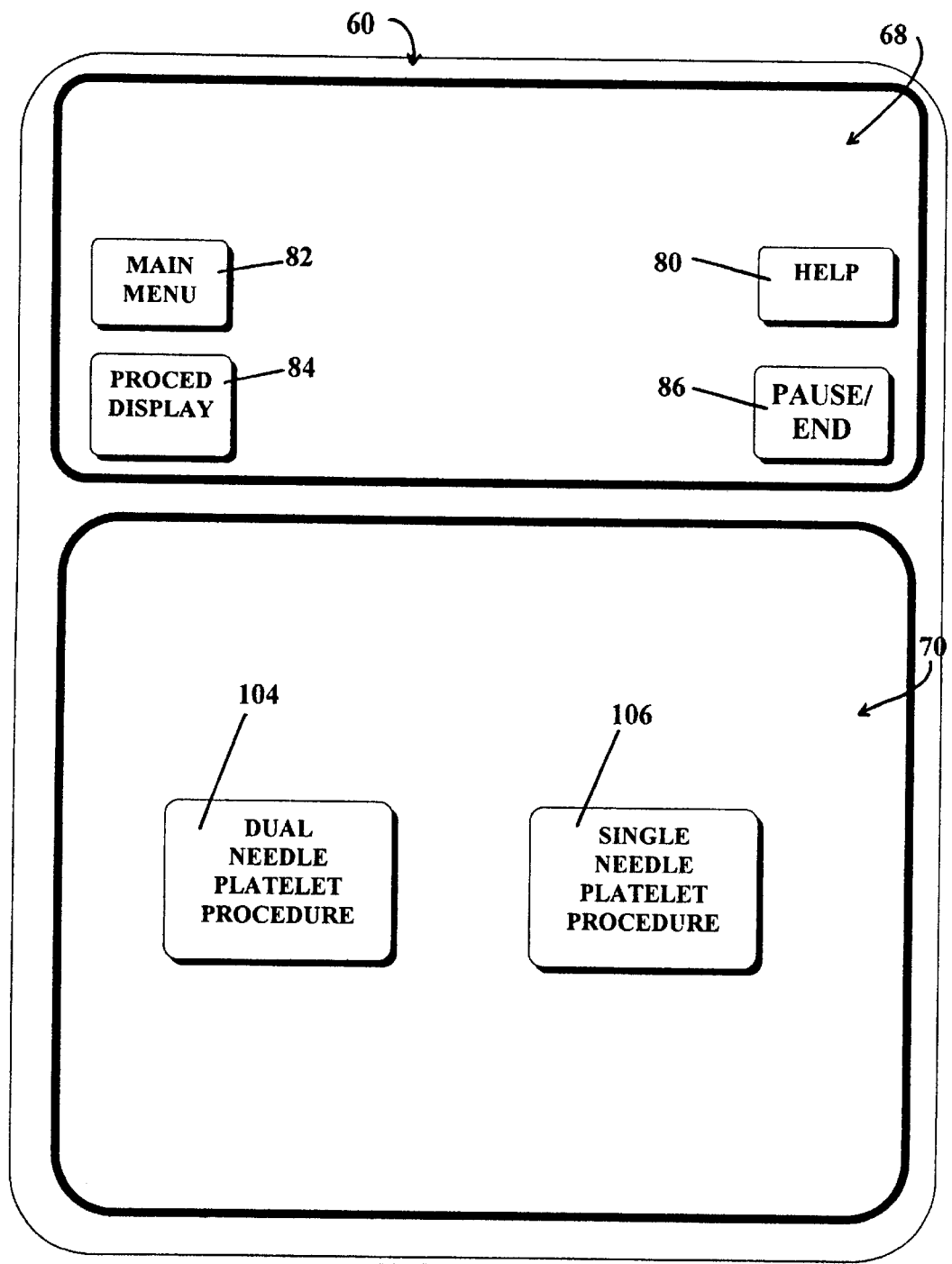
FIG. 10 is a view of the dual region interface, showing the Select Procedures SubMenu in the working region of the interface screen.

FIG. 10 shows the condition of the dual region interface screen 60, after the operator has selected the CHOOSE PROCEDURE button field 94 in the working region 70. The status region 68 shows no change. The working region 70 shows in button fields 104 and 106 the clinical procedure applications resident in the application control manager 46. In the illustrated embodiment, a button field 104 labeled the Dual Needle Platelet Procedure is shown for activating the application A1. Additional button fields would also exist (for example, a Single Needle Platelet Procedure button field 106, as shown) equal in number to the number of procedure applications residing in the application control manager 46.

Figure 11:
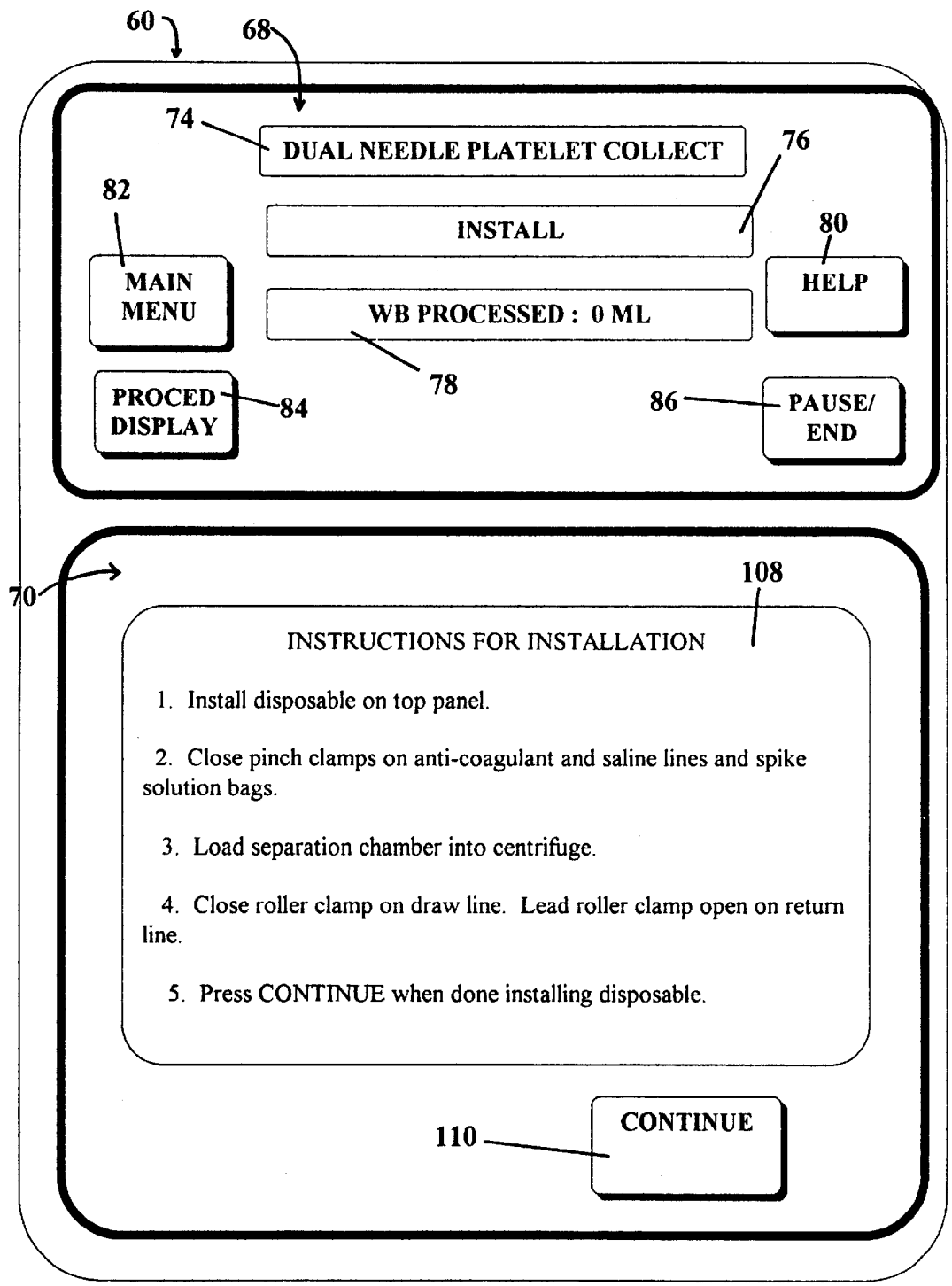
FIG. 11 is a view of the dual region interface, showing the installation instructions for the install mode in the working region of the interface screen.

FIG. 11 shows the condition of the dual region interface screen 60, after the operator has selected the Dual Needle Platelet button field 104 in the working region 70. The status region 68 shows in the MAJOR MODE field 74 that the Dual Needle Platelet Collection Procedure has been selected. The Status region 68 also shows in the MINOR MODE field 76 that the procedure is in the install mode. The status region shows in the WB PROCESSED FIELD 78 that no whole blood has been collected yet. The working region 70 shows in the textual field 108 instructions for the operator to follow in installing the disposable elements on the hardware elements. The working region 70 also shows a touch activated CONTINUE button field 110 which, when touched, causes the instructions in the textual field 108 to progress, taking the operator stepwise through the installation procedure until complete.

The MINOR MODE field 76 in the status region 68 changes as the activated procedure progresses through successive modes including a check of hardware functionality, priming of the fluid flow paths to remove air, procedure start-up, and venipuncture tasks, either automatically or with the assistance of the operator. The textual field 108 in the working region 70 also changes to display information, as appropriate, to prompt the operator to take steps to aid in accomplishing these tasks. In all other respects, the other visual aspects of the status region 68 and working region 70 remain unchanged.

Figure 12:
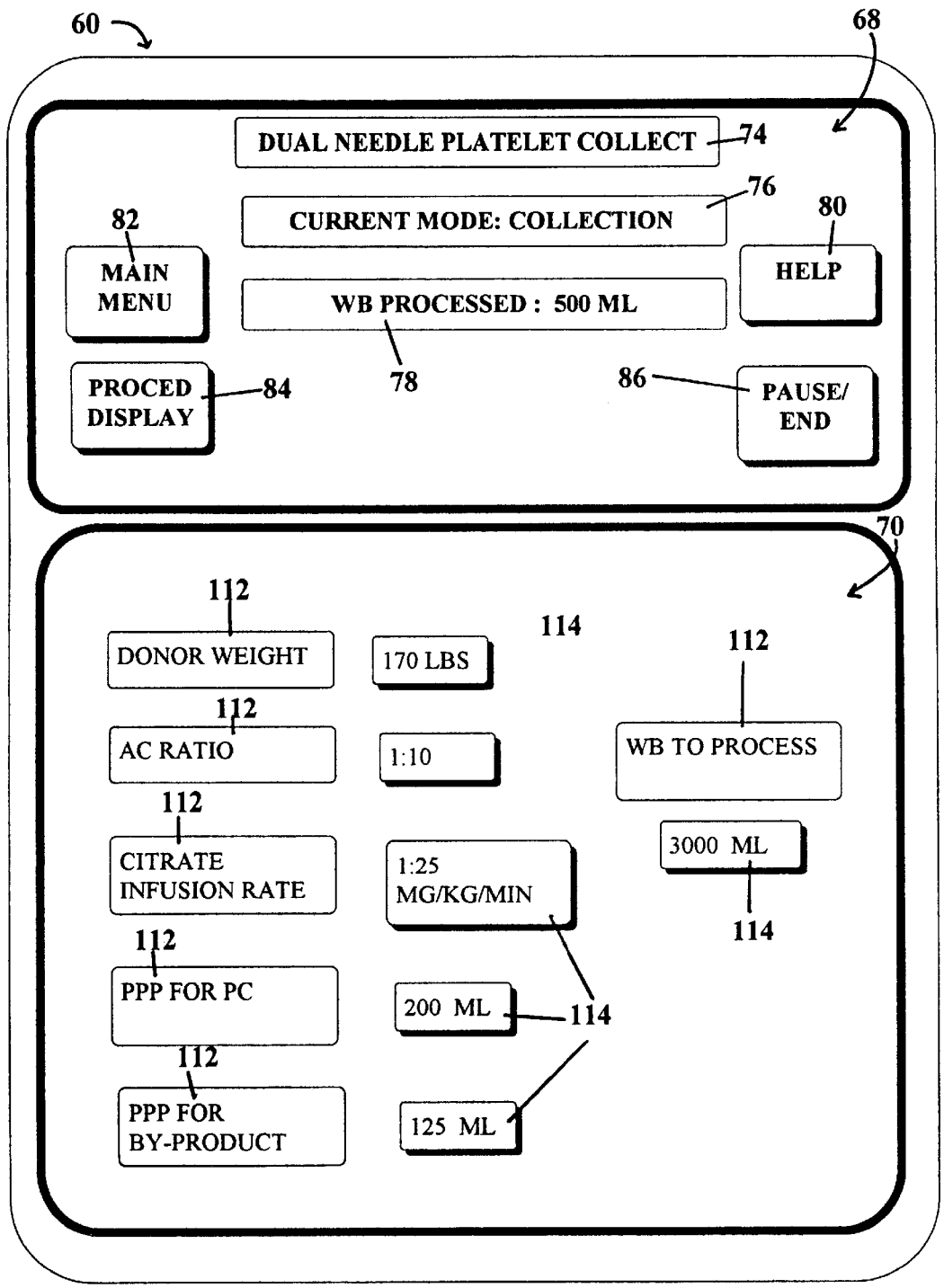
FIG. 12 is a view of the dual region interface, showing the detailed procedures display for the collection mode in the working region of the interface screen.

FIG. 12 shows the condition of the dual region interface screen 60, when the procedure enters the collection mode. During the collection mode, whole blood is drawn from the donor, centrifugally separated into component parts, and its components either returned to the donor or collected, as earlier described.

The Status region 68 continuously shows in the MINOR MODE field 76 that the procedure is in the collection mode. The status region continuously shows in the WB PROCESSED FIELD 78 the volume of WB drawn from the donor. The location and attributes of the other button fields 80/82/84/86 remain unchanged, unless the procedure changes operational mode, at which time the MINOR MODE field 76 will change to reflect this mode change.

The working region 70 continuously shows in an array of prescribed textual block fields 112 and associated prescribed touch activated button fields 114 selected field values detailing the progress of the ongoing procedure.

The type of information selected by the procedure application for display as a field value in the working region 70 during the collection mode can vary. In the illustrated embodiment, the block fields 112 list by way of example the donor weight, the anticoagulant (AC) ratio, the rate of infusing citrate carried by the PPP returned to the donor, the volume of PPP collected for resuspending collected PC, the amount of additional PPP collected as a by-product, and the amount of whole blood yet to be processed to meet the PC yield selected for the procedure. The associated button fields 114 contain the current status of these operational factors, which are displayed as field values within the button fields 114.

Field values in the button field 114 change to reflect changes in the current status, when they occur. For example, the amount of WB to be processed decrements over time toward zero. When the WB to process button field 114 is zero, the application prompts the operator to begin the flush and reinfusion mode.

Figure 13:
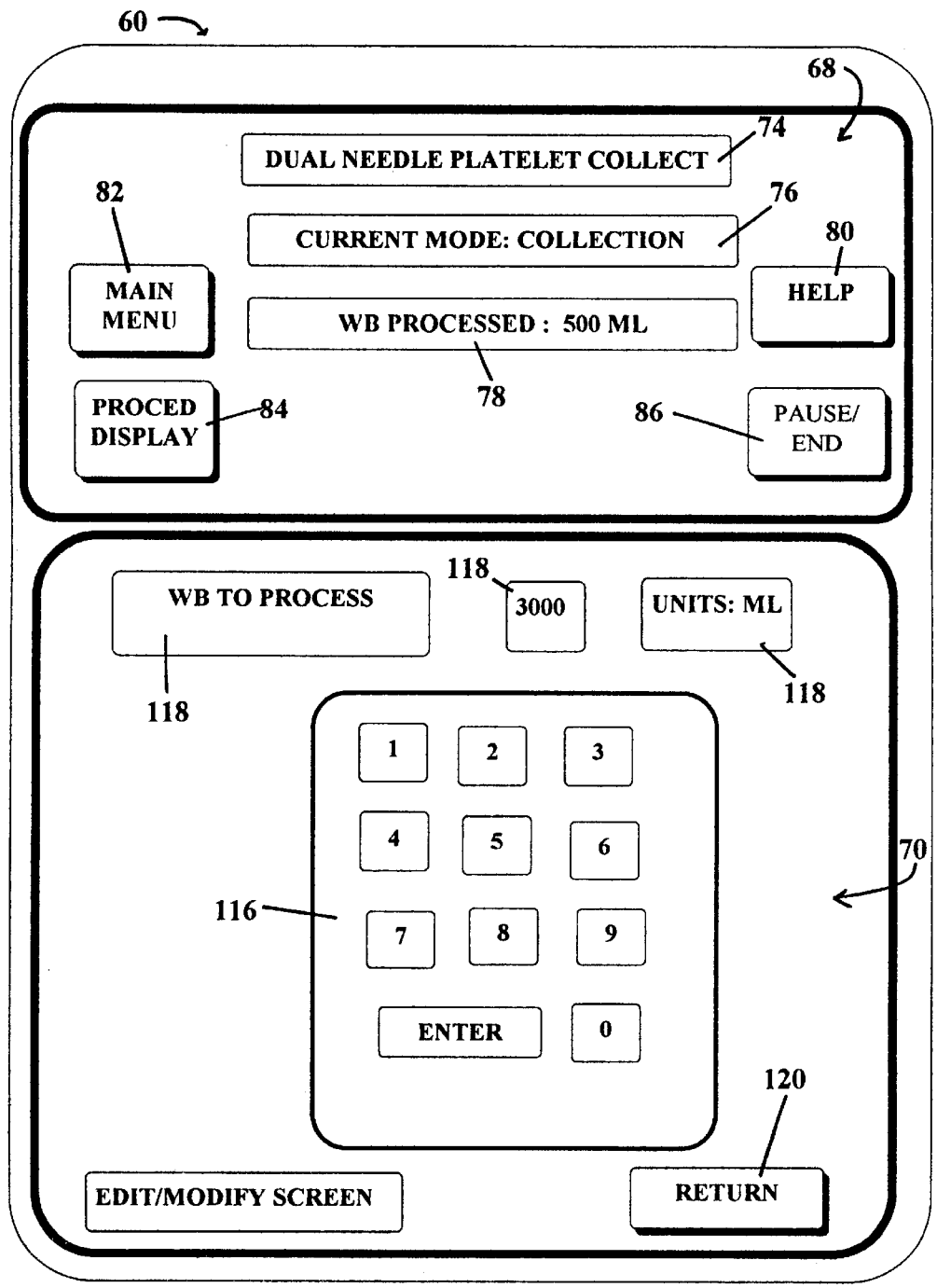
FIG. 13 is a view of the dual region interface, showing the edit/modify screen for the detailed procedures display in the working region of the interface screen during the collection mode.

In the illustrated and preferred embodiment, the operator can, by touch selecting a given button field 114, modify the displayed field value. FIG. 13 shows the condition of the display screen 60 when, for example, the operator touch selects the WB TO PROCESS button field 114 in the working region 70 to change the volume of whole blood to be processed during the procedure. The working region 70 display changes to display a touch activated numeric keypad 116, along with block fields 118 showing the field value to be changed, it present value, and the units in which it is expressed. By touch activating the keypad 116, the operator changes and enters the new value, then selects the touch activated Return button field 120 to return to the working display 70 shown in FIG. 12. The field value in the WB TO PROCESS button field 114 will reflect the new field value.

As FIG. 13 shows, as the working region 70 display changes to accommodate the edit/modify procedure just described, the status region 68 display remains visible and unchanged, except to reflect changes in the volume of whole blood processed during the edit/modify procedure or any change in operational mode called for by the activated application.

Figure 14:
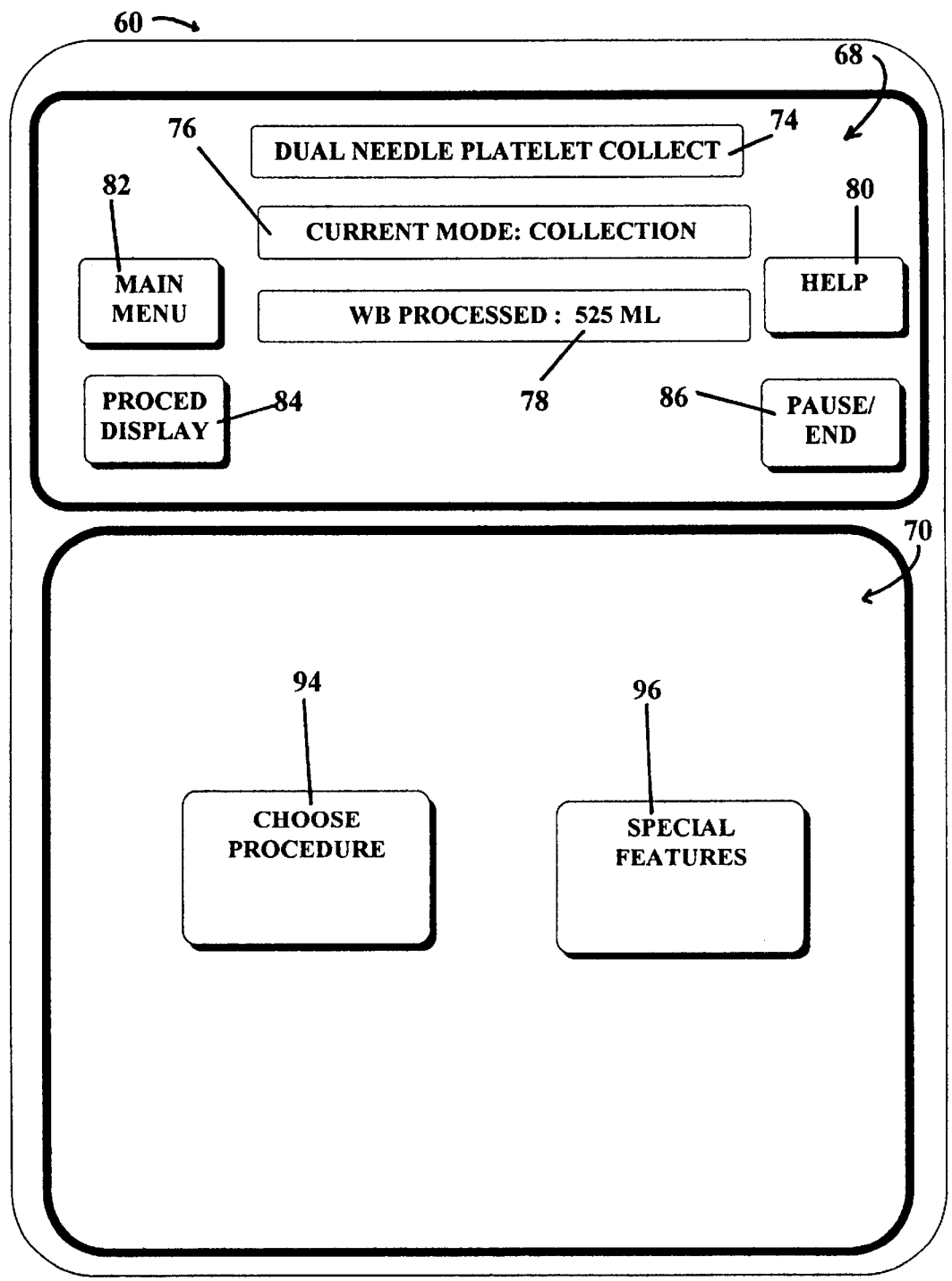
FIG. 14 is a view of the dual region interface, showing the Main Menu in the working region of the interface screen during the collection mode.

At any time the operator may choose to return to the main menu by touch selecting the MENU button field 82 in the status region 68. FIG. 14 shows the condition of the display screen 60 should the operator make this choice after having completed the exit/modify procedure just described.

As FIG. 14 shows, the working region 70 of the screen changes to show the Main Menu. The status region 68 display remains visible and unchanged, reflecting the status information at the time the MENU button field 82 was activated by the operator, except to reflect ongoing changes in the volume of blood processed (as a comparison of FIG. 14 to FIG. 12 shows) or a change in operational mode.

Figure 15:
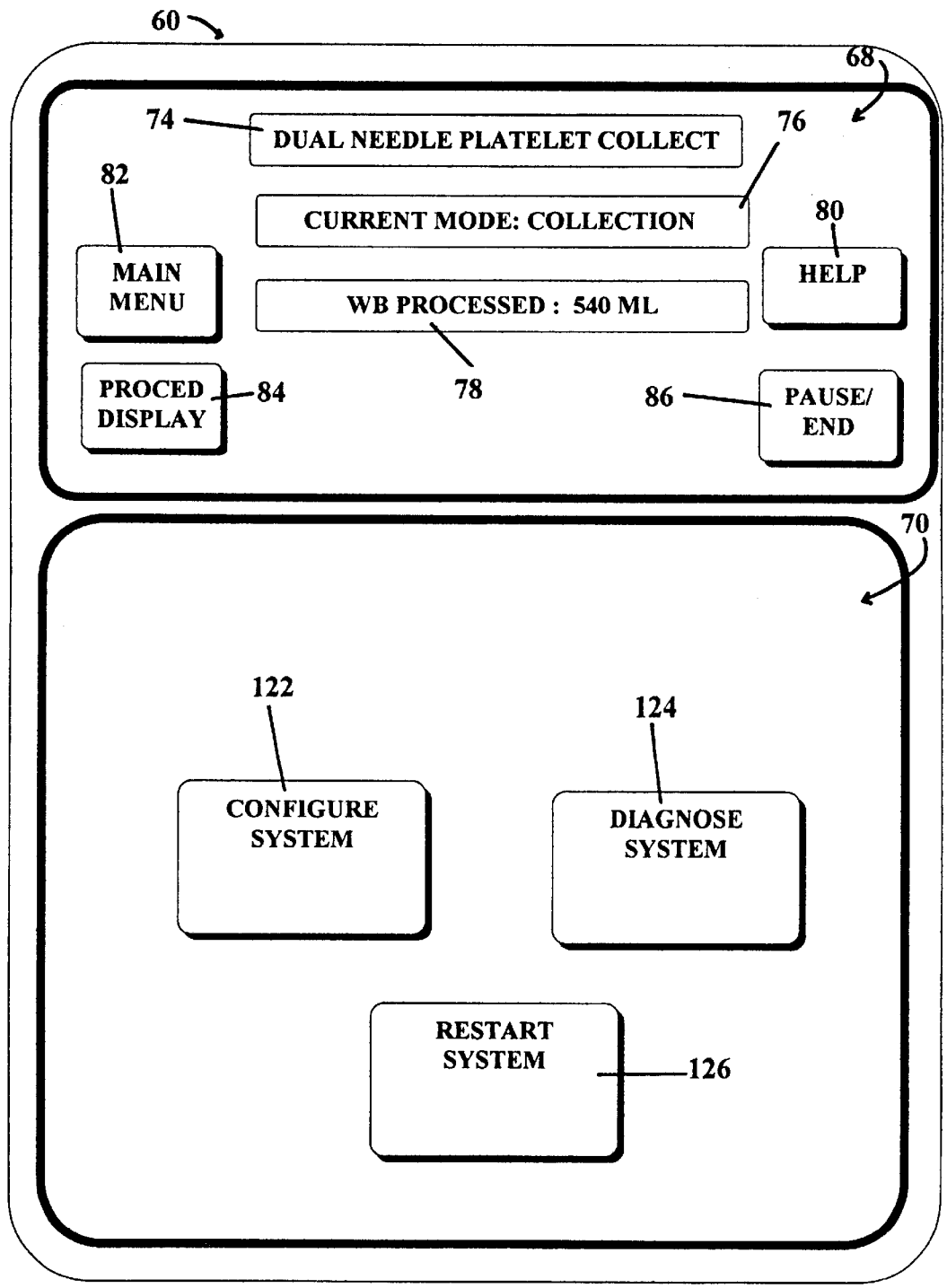
FIG. 15 is a view of the dual region interface, showing the Special Features SubMenu in the working region of the interface screen during the collection mode.

The operator can next proceed to touch select the Special Features button field 96, if desired. FIG. 15 shows the condition of the display screen when this selected is made. As FIG. 15 shows, the working region 70 of the screen 68 changes to show the Features Submenu. The Features Submenu lists in an array of touch selectable button fields 122, 124, and 126 the non-procedure specific applications administered by the application control manager 46. Touch button field 122 activates the Configure System Procedure Application A2. By way of further example, FIG. 15 assumes that additional non-clinical procedural applications are also resident in the application control manager 46, such as the diagnosis application (which touch button field 124 activates) and system restart application (which touch button field 126 activates), as previously discussed.

As FIG. 15 shows, the status region 68 display remains visible and unchanged as the working region 70 display changes to show the Features Submenu. The status region 68 continues to reflect the status information at the time the SPECIAL FEATURES button field 96 was activated by the operator, except to reflect ongoing changes in the volume of blood processed (as a comparison of FIG. 15 to FIG. 14 shows) or changes in the operational mode.

The operator may proceed to touch select a given button field 122, 124, 126 in the working region 70 shown in FIG. 15. The selected button field will activate the associated application. Meanwhile, the status region 68 remains visible and unchanged, except to reflect status changes in the information fields it contains.

At any time, and regardless of the active display presently in the working region 70, the operator may choose to again view detailed status information about the clinical procedure then being implemented (as shown in the MINOR MODE field 76). To do so, the operator need only to touch select the PROCEDURE DISPLAY field button 84, which remains continuously visible and accessible at all times to the operator in the status region 68. The working region 70 display returns to the format and attributes shown in FIG. 12 (if the process is still in the collection mode), or whatever the format or attributes of the procedure display is for the mode identified in the MINOR MODE field 76.

In this way, the status region 68 keeps the operator continuously informed as to the "big picture" as the working region 70 changes to provide access to the details of processing. The status region 68 also provides the means for the operator to quickly jump through the multiple-level menu structure of the interface 58, to attend to details on one menu level, without necessarily moving stepwise up and down the menu structure and without losing the ability to, on command, immediately jump between higher and lower menu levels.

The MINOR MODE field 76 changes to reflect mode changes made under the control of the activated application. After collection ends (i.e., when the designated WB TO PROCESS field value shown in FIG. 12 decrements to zero), the procedure prompts the operator to enter the RBC flush and reinfusion mode, during which residual RBC are flushed and returned to the donor. The procedure then enters a Procedure Wrap Up mode, in which the operator is instructed to remove the disposable components.

C. Abnormal Operational Conditions (i) Detection

Each procedure application (see FIG. 6) defines abnormal functional and operational states that require operator awareness and/or operator intervention. The procedure application A1 processes status data received from the instrument manager 50 to determine whether any current operating condition constitutes a prescribed abnormal functional state. If so, the application control manager 46 issues prescribed commands to notify the operator through the user interface 58 and, under certain conditions, suspend system operation.

As earlier described, the MPU 44 also includes the condition manager 56 to provide fail-safe support to error detection functions of the application control manager 46. It should be appreciated that, alternatively, the condition manager 56 can reside in an auxiliary processing unit (APU) (for example, a second type 68030 microprocessor), or partly in the MPU 44 and partly in an APU.

The condition manager 56 contains a list defining abnormal functional and operational states. Some of the defined states in the condition manager 56 are the same as the states defined in the application control manager 46, while others are independent cross checks of hardware control commands and status data to verify hardware integrity that only the condition manager 56 undertakes.

The condition manager 56 monitors the flow of data between the instrument manager 50 and the peripheral hardware controllers 54 (shown in FIG. 2) to determine whether any current operating condition meets the criteria defined for an abnormal functional state. Where possible, the condition manager 56 preferable includes a time-out period for conditions that the application control manager 46 also monitors, to thereby allow the application control manager 46 a period of time to correct the abnormal state.

Figure 6:
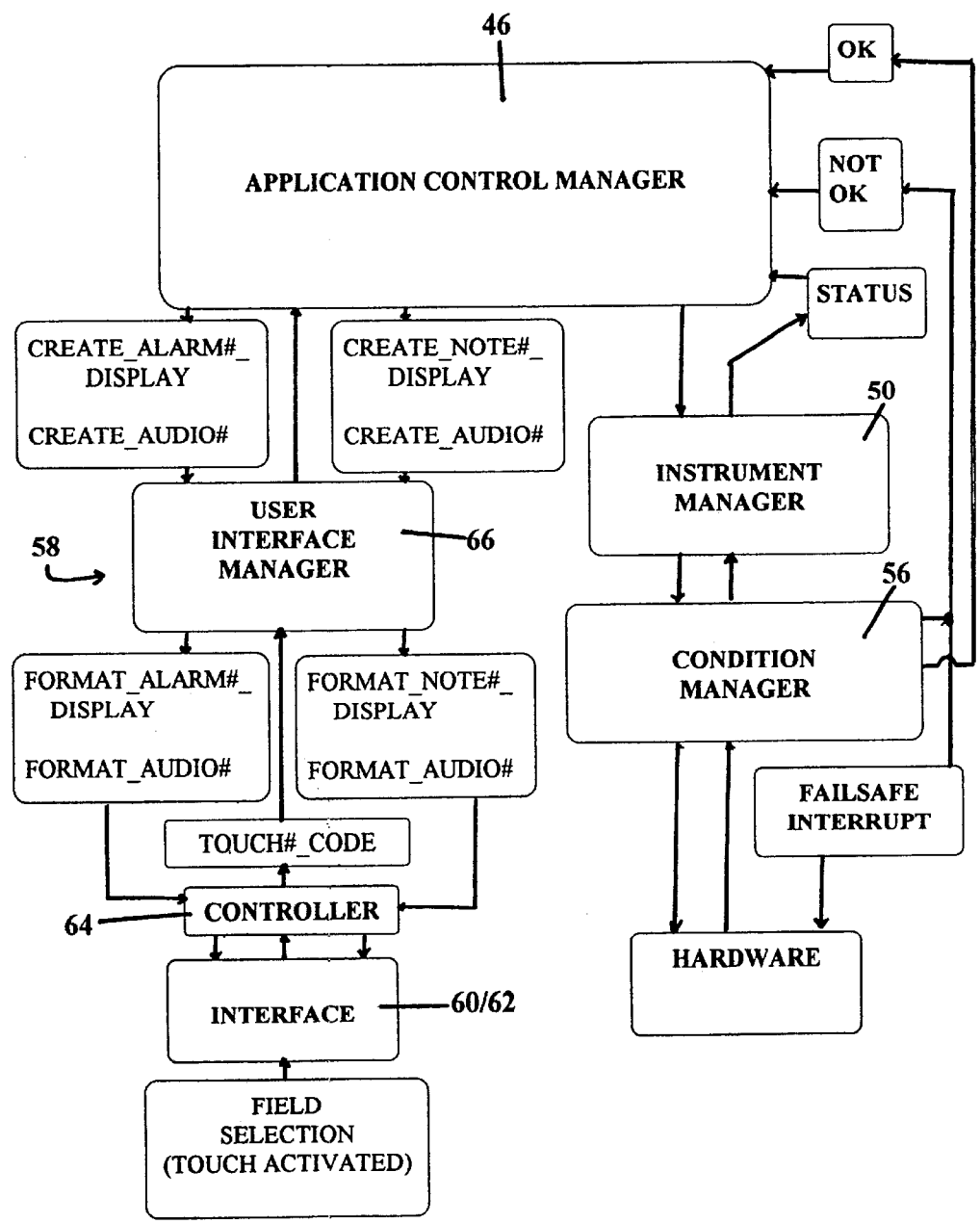
FIG. 6 is a diagrammatic view of the detection and display of abnormal function conditions by the controller shown in FIGS. 2 and 3.

As FIG. 6 shows, the condition manager 56 continuously sends an OK_State status to the application control manager 46 as long as no current operating condition constitutes a defined abnormal functional state, or as long as the time-out period for a sensed abnormal functional state, if applicable, has not lapsed.

When the condition manager 56 detects a current operating condition that meets the criteria defined for an abnormal functional state, and if the time-out period, if applicable, has lapsed, the condition manager 56 sends a Not_OK_State# status to the application control manager 46. The Not_OK-State# status identifies to the application control manager 46 the abnormal condition detected. Upon receipt of the Not_OK_State# status from the condition manager 56, and regardless whether the activated procedure application also detects the same abnormal functional state, the application control manager 46 issues prescribed commands to notify the operator through the user interface 58.

Upon issuing a Not_OK_State# status, the control manager 56 goes fail-safe, suspending system operation and interrupting all further communication between the application control manager 46 and the peripheral controllers 52 until the abnormal state is corrected.

(ii) classification

In the preferred embodiment, the application control manager 46 categorizes defined abnormal functional and operational states either as an alarm condition or as an attention condition. The alarm conditions comprise functional and operational states requiring immediate operator intervention. The attention conditions comprise functional and operational conditions that may be transient and self-correcting over time, or that otherwise do not require immediate operator intervention. In the preferred embodiment, the application control manager 46 automatically upgrades an attention condition that remains uncorrected for a prescribed period of time after detection (for example, 2 minutes) to an alarm condition. The application control manager 46 also automatically treats a Not_OK_State# status from the condition manager 56 as an alarm condition.

Examples of abnormal operational states that can be treated as alarm conditions include pump motor direction error; pump motor speed error; liquid spill detected indide the centrifuge; centrifuge rotor imbalance; control voltage power failure; centrifuge door open; centrifuge door not locked; empty anticoagulant container.

Examples of abnormal operational states that can be treated as alarm conditions include temperature in centrifuge above limit; weight scale limits exceeded; and anticoagulant level low.

As FIG. 6 shows, upon detection of a condition that represents an alarm condition, the application control manager 46 generates and transmits a prescribed Create_Alarm#_Display command to the interface manager 66. Likewise, upon detection of condition that represents an attention state, the application control manager 46 generates and transmits a prescribed Create_Note#_Display command to the interface manager 66.

Upon receipt of a prescribed Create_Alarm# or _Note#_Display, the interface manager 66 examines the ROM-based table structures and the RAM-based status structures to create or update the display codes to implement the designation display and audio through the interface controller 64 using the interface screen 60 and audio device 62.

In the illustrated and preferred embodiment, the interface manager 66 places all displays generated in response to Create_Alarm#_Display or Create_Note#_Display commands initially in the status region 68 of the interface screen 60, as FIG. 4 shows. The interface manager 66 reserves the top position on the left and right sides and the bottom center position of the status region 68 for the alarm and note fields 88/90/92. These positions on the status region 68 remain free of any display character or indicia in the absence of a sensed alarm or attention condition.

(i) Warning Alarm Interface

In response to a Create_Alarm#_Display command from the activated procedure application, the interface manager 66 creates the touch selectable, button field 88 (see FIG. 4) on the right side, top position, of the status region 68. In the preferred implementation, in an alarm state, the button field 88 is colored red (the international alarm color) and contains the word "Warning" or some other word or words to denote a sense of urgency.

The interface manager 66 also creates the touch selectable mute button field 90 on the left side, top position, when an alarm state is active. Touch selection of the mute button field 90 turns off a prescribed time period any audible alarm associated with the alarm state.

With the creation of the button field 88, the interface manager 66 creates the alarm block field 92 at the bottom of the status region 68. In an alarm state, the block field 92, also preferably colored red and bar-shaped, contains a description of the warning condition of appropriate length.

Figure 7:
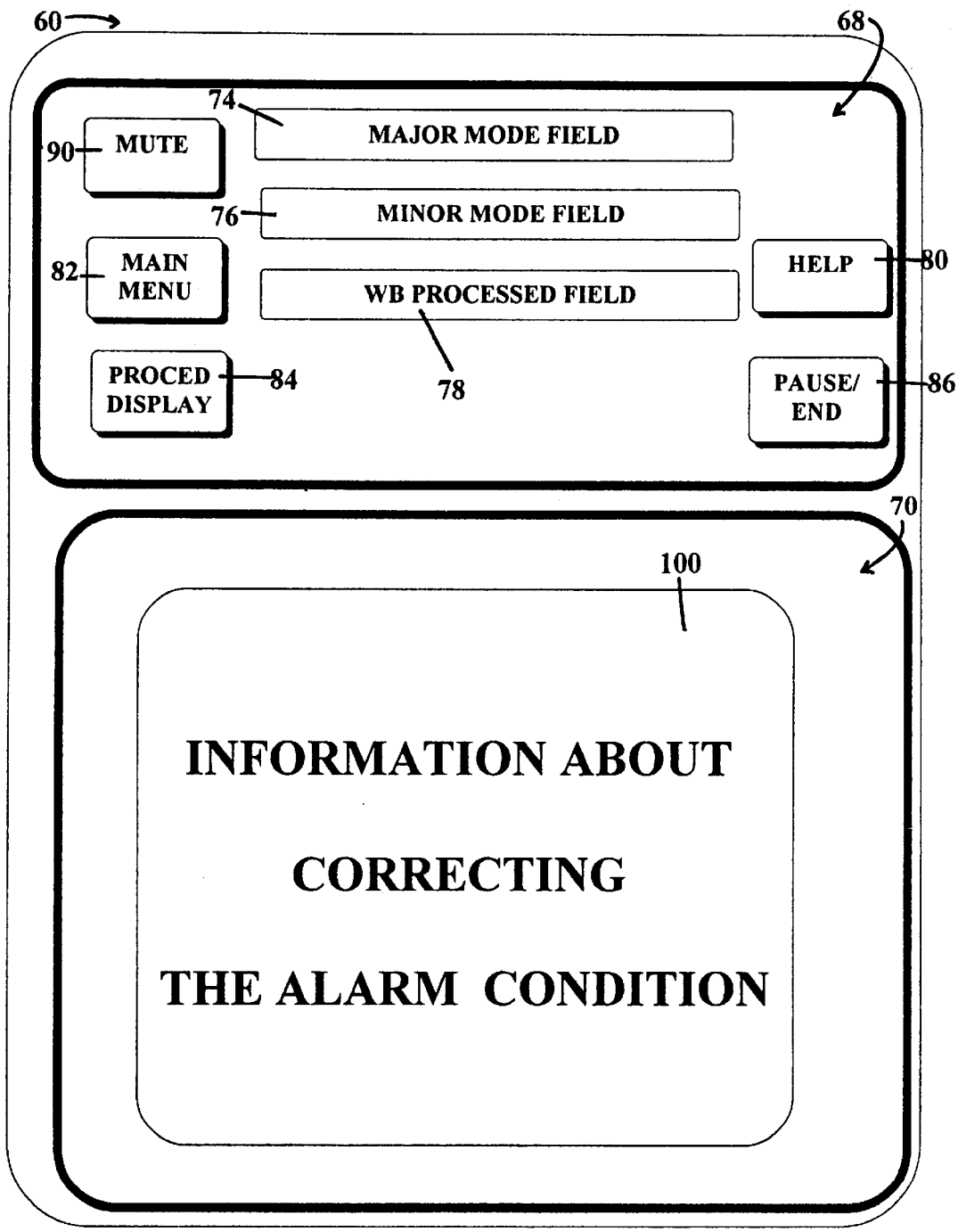
FIG. 7 is a view of the dual region interface in an alarm condition.

When the operator touch selects the warning alarm button field 88 (as FIG. 7 shows), the interface manager 66 removes the button field 88 and the block field 92 from the status region 68 and displays in a textual field 100 in the working region 70 more detailed information regarding the appropriate responses for the operator to follow in correcting the sensed alarm state. Working through the interface manager 66, the alarm state of the activated procedure application maintains control over the working region 70 of the interface, allowing no display except those relating to the alarm state and associated corrective measures to be active, until the condition manager 56 and the application control manager 46 sense the removal of the alarm state.

(ii) Note Alarm Interface

In response to a Create__Note#-Display command from the activated procedure application, the interface manager 66 creates the touch selectable, button field 88 on the right side, top position, of the status region 68 (see FIG. 4). In the preferred implementation, in an attention state, the button field 88 is colored yellow or another cautionary color distinguishable from the color of the button field 88 in an alarm condition. The button field 88 contains the word "Note" or some other cautionary word or words readily distinguishable from the word contained in the field 88 when in an alarm state.

The interface manager 66 also creates the touch selectable mute button field 90 on the left side, top position, when an attention state is active. Touch selection of the mute button field 90 turns off a prescribed time period any audible alarm associated with the attention state.

With the creation of the note alarm button field 88, the interface manager 66 creates the block field 92 at the bottom middle of the status region 68. The block field 92, preferably colored the same color as the note alarm button field and bar-shaped, contains a description of the attention condition of appropriate length.

When the operator touch selects the note alarm button field 88, the interface manager 66 removes the block field from the status region 68 and displays in the textual field 100 (see FIG. 7) in the working region 70 more detailed information and regarding the appropriate responses for the operator to follow in correcting the sensed attention state, if appropriate. Working through the interface manager 66, the attention state of the activated procedure application maintains control over the working region 70 of the interface, allowing no display except those relating to the attention state and associated corrective measures to be active, until the condition manager 56 and the application control manager 46 sense the removal of the attention state.

In the preferred embodiment, the alarm/note fields 88 and 92 relate only to a single alarm or note condition at the same time. There are never multiple displays of these fields at a given time, even when multiple Create__Alarm#__Display and/or Create__Note#__Display commands are received. In this circumstance, the user interface manager 66 stacks the multiple commands in an alarm queue and an attention que as received. The user interface manager 66 and implements the commands for display one at a time, on a first-in, first-out basis, except that an alarm state takes precedence over any attention state. Touch activating the active alarm/note button field 88 to open the associated alarm/note textual field 100 in the working region 70, opens the alarm/warning fields 88 and 92 relating to the next prioritized alarm/attention command in the status region 68. Thus, in the case of multiple pending alarm/attention conditions, as the operator works in the working region 70 to remove one condition, the status region 68 informs the operator of another condition that next requires attention.

The following example illustrates the operation of the interface when an alarm/attention condition is sensed.

EXAMPLE

Figure 16:
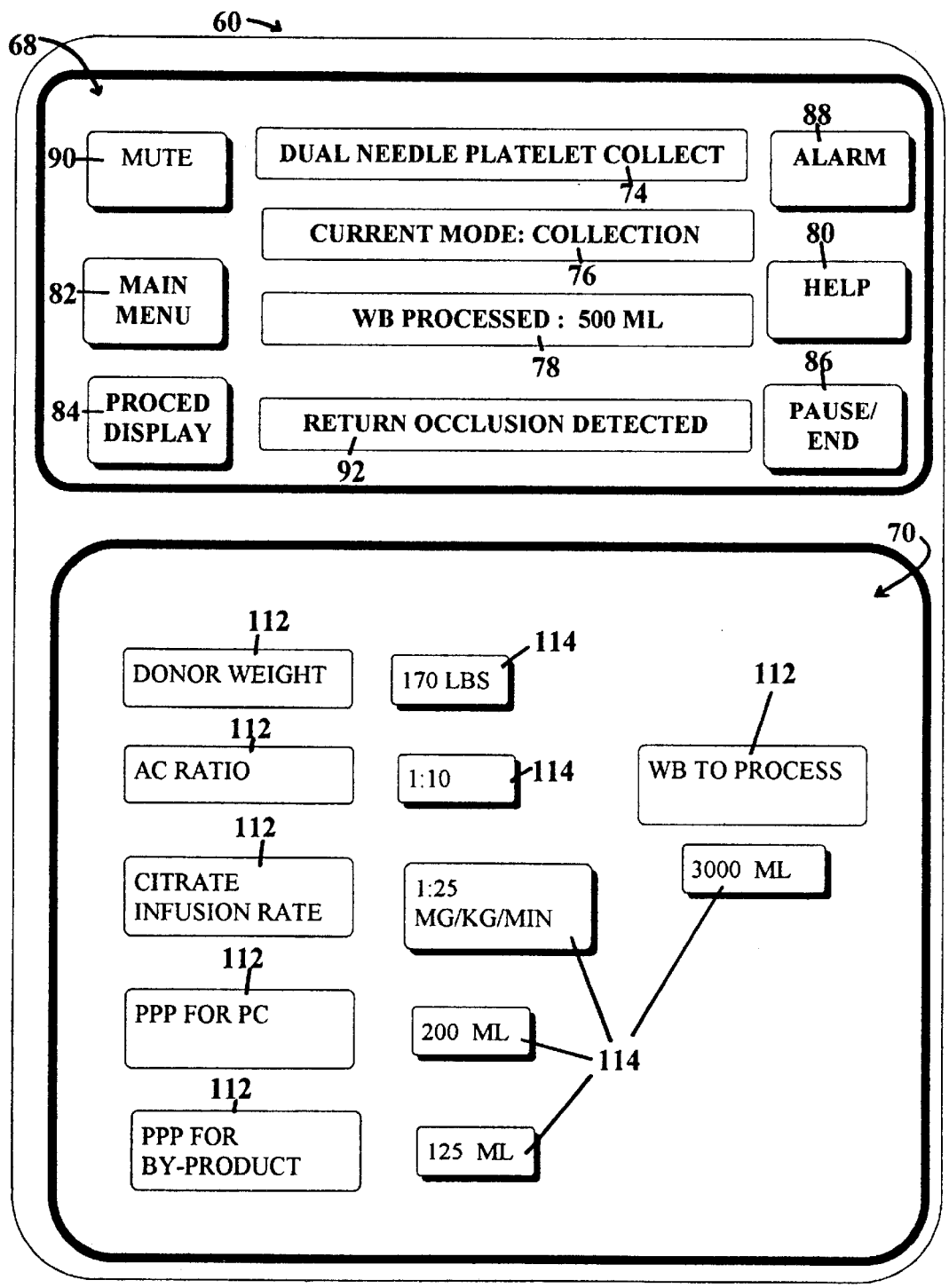
FIG. 16 is a view of the dual region interface, with the detailed procedures display for the collection mode in the working region, and a return occlusion alarm in the status region.

FIG. 16 shows the condition of the interface screen 60 should an occlusion in the tubing branch 40 (see FIG. 1) returning RBC and PPP to the donor be sensed by the application control manager 46 in the manner described above. FIG. 16 assumes that, at the time that occlusion is detected, the screen 60 had a display like that shown in FIG. 12.

As FIG. 16 shows, the display in the status region 68 changes to include the button field 88, which is displayed in red to designate an alarm state (as contrasted with an attention state). The status region 68 also changes to show the block field 92, which is also in red, and which contains text identifying the nature of the alarm (Return Occlusion Detected). The status region 68 also shows the MUTE button field 90, allowing the operator to mute any audible alarm called for by the application control manager 46 for the identified alarm state. The working region 70 continues to show the display that was active at the time the alarm condition was detected.

Figure 17:
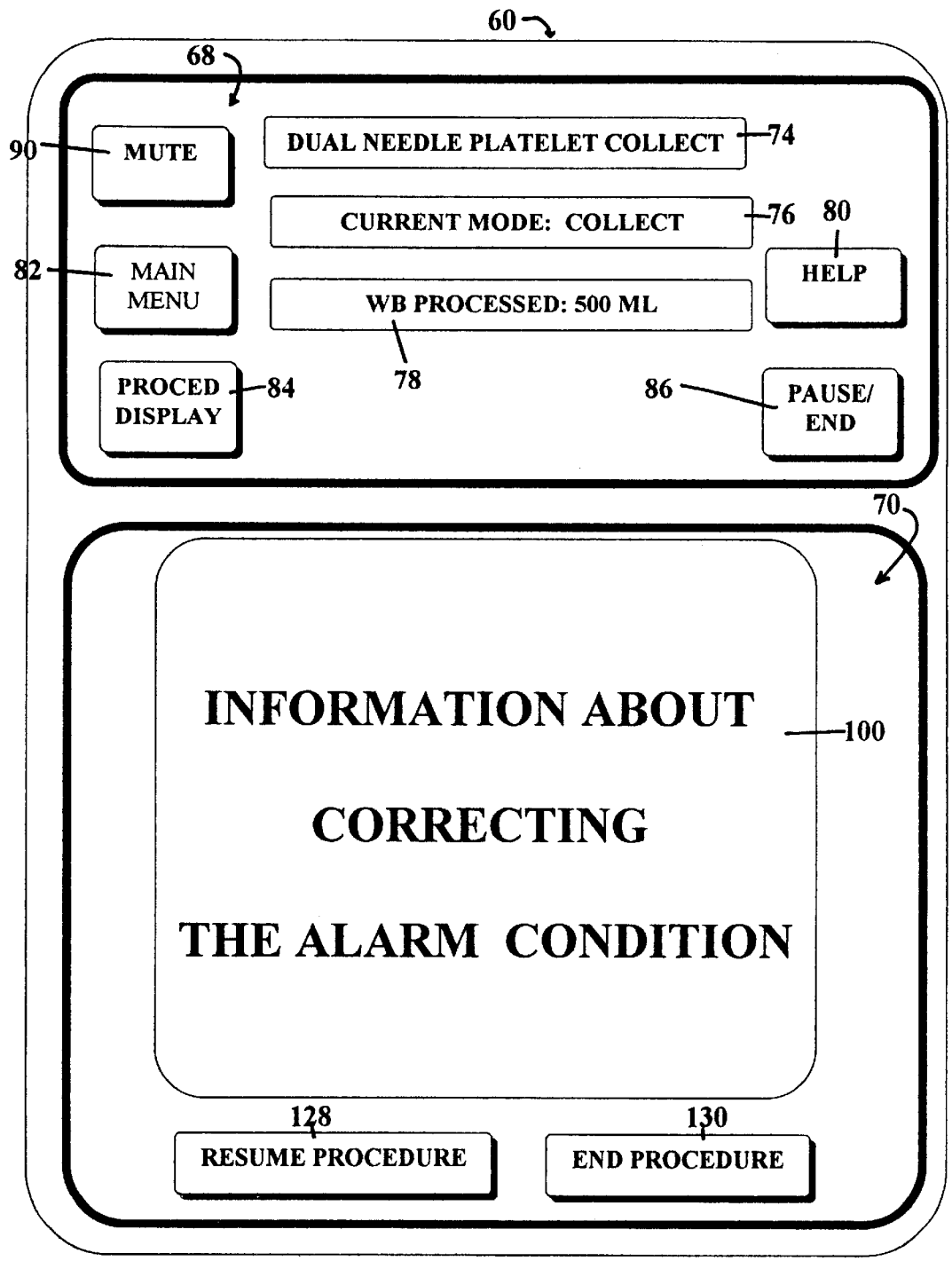
FIG. 17 is a view of the dual region interface, with the instructions for correcting the return occlusion alarm in the working region during the collection mode.

FIG. 17 shows the condition of the screen 70 after the operator touch selects the alarm field button 88. The display in the status region 68 changes by the removal of the alarm button field 88 and associated block field 92. The display in the working region 70 changes to show the text block field 100 (also shown in FIG. 7) containing information about the detected alarm condition and suggested ways of correcting it. The working region 70 also includes touch selected button fields 128 and 130. The button field 128 allows the operator to resume the procedure, once the alarm condition is corrected. The button field 130 gives the operator the option of ending the procedure.

Upon correcting the alarm condition and touch selection of the button field 128, the working region 70 of the display screen 60 returns to the display that was active at the time the alarm condition was first displayed, which in the illustrated embodiment would be FIG. 12.

The specific computer code used for implementing the applications A1–A3, the application control manager 46, the instrument manager 56, condition manager 56, the interface manager 66, and the interface controller 64 depends upon the computer language being used and the preferences of the programmer. The procedures and commands described in this specification can all be written by normally skilled programmers in various conventional languages, like C; Pascal; PLM; ADA; and multiple tasking BASIC, based upon the descriptions provided herein.

Appendix A includes illustrative functional requirements in a preferred implementation of an interactive user interface that embodies features of the invention.

Various features of the invention are set forth in the following claims.

We claim:

1. A blood processing system including
an array of hardware elements,
an application control manager including at least one procedure application that lists procedural steps to carry out a predetermined blood processing procedure, and a first program element that defines functional steps for actuating the hardware elements to carry out the procedural steps and generates prescribed abstract function selection commands based upon the defined functional steps,
an instrument manager communicating with the application control manager and including a second program element that generates specific hardware selection commands in response to receiving the function selection commands generated by the first program element,
a peripheral control element communicating with the hardware elements and with the instrument manager for actuating the hardware elements in response to receiving the hardware selection commands generated by the second program element, and the instrument manager including an output for transmitting to the application control manager at least one processing status value that changes over time as the hardware elements are actuated in response to the hardware selected commands.

2. A system according to claim 1 wherein the application control manager includes a third program element that generates a display field value reflecting the at least one processing status value and prescribed abstract create display commands defined by the one procedure application, and further including an interface manager communicating with the application control manager and including a fourth program element for generating specific format display commands in response to receiving the display field value and the abstract create display commands generated by the third program element.

3. A system according to claim 2 further including an interface controller communicating with the interface manager and including a fifth program element that formats a display based upon the specific format display commands generated by the fourth program element.

4. A system according to claim 3 further including an interface device coupled to the interface controller and including the display formatted by the fifth program element.

* * * * *